United States Patent
Takahashi

(10) Patent No.: US 10,280,443 B2
(45) Date of Patent: May 7, 2019

(54) METHOD FOR PURIFYING TARGET PROTEIN

(71) Applicant: SYSMEX CORPORATION, Kobe-shi, Hyogo (JP)

(72) Inventor: Ryo Takahashi, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 58 days.

(21) Appl. No.: 15/480,719

(22) Filed: Apr. 6, 2017

(65) Prior Publication Data

US 2017/0292140 A1  Oct. 12, 2017

(30) Foreign Application Priority Data

Apr. 7, 2016  (JP) ................. 2016-077129

(51) Int. Cl.
| | | |
|---|---|---|
| *C12P 21/06* | (2006.01) | |
| *C12N 15/62* | (2006.01) | |
| *B01D 15/08* | (2006.01) | |
| *C07K 1/18* | (2006.01) | |

(52) U.S. Cl.
CPC .............. *C12P 21/06* (2013.01); *B01D 15/08* (2013.01); *C07K 1/18* (2013.01); *C07K 2319/00* (2013.01); *C07K 2319/20* (2013.01); *C07K 2319/50* (2013.01); *C07K 2319/61* (2013.01)

(58) Field of Classification Search
CPC ............ C12P 21/06; C07K 7/06; C12N 15/62
See application file for complete search history.

(56) References Cited

U.S. PATENT DOCUMENTS

| | | | |
|---|---|---|---|
| 4,851,341 A | 7/1989 | Hopp et al. | |
| 7,462,463 B1 * | 12/2008 | Tirrell | C12N 15/62 435/7.9 |
| 2002/0169125 A1 * | 11/2002 | Leung | C07K 7/06 424/85.2 |

OTHER PUBLICATIONS

ResearchGate. 2012; Trouble separating target protein from cleaved GST due to similar size and pI, on the web at www.researchgate.net/post/Trouble_separating_target_protein_from_cleave_GST_due_to_similar_size_and_pI.*
Fuchs et al. 2005. Polyarginine as a multifunctional fusion tag. Protein Science 14: 1538-1544.*
Lan et al. 2011; An improved nonchromatographic method for the purification of recombinant proteins using elastin-like polypeptide-tagged proteases. Analytical Biochemistry. 415: 200-202.*
Waugh. 2011; An overview of enzymatic reagents for the removal of affinity tags. Protein Expr. Purif. 80(2): 283-293.*
K. Stubenrauch, et al., "Purification of a viral coat protein by an engineered polyionic sequence", Journal of Chromatography B, 2000, pp. 77-84, vol. 737.
Mayank Saraswat, et al, "Preparative Purification of Recombinant Proteins: Current Status and Future Trends", BioMed Research International, 2013, 18 pages, vol. 2013, Article ID 312709.

* cited by examiner

*Primary Examiner* — Karen Cochrane Carlson
(74) *Attorney, Agent, or Firm* — Sughrue Mion, PLLC

(57) ABSTRACT

Disclosed is a method for purifying a target protein, comprising steps of: bringing a fusion protein containing an amino acid sequence of a peptide tag, an amino acid sequence of a cleavable site of a protease and an amino acid sequence of a target protein, into contact with the protease in a solution, to cleave the peptide tag from the fusion protein; and bringing the solution containing the peptide tag, the target protein and the protease into contact with an ion exchange resin to separate the target protein and the peptide tag, thereby acquiring a solution containing the target protein, wherein, in the fusion protein, the amino acid sequence of a cleavable site of the protease exists between the amino acid sequence of the peptide tag and the amino acid sequence of the target protein, and the peptide tag is polyanionic or polycationic.

14 Claims, 11 Drawing Sheets
Specification includes a Sequence Listing.

METHOD FOR PURIFYING TARGET PROTEIN

CROSS REFERENCE TO RELATED APPLICATIONS

This application claims priority from prior Japanese Patent Application No. 2016-077129, filed on Apr. 7, 2016, entitled "METHOD FOR PURIFYING TARGET PROTEIN", the entire contents of which are incorporated herein by reference.

TECHNICAL FIELD

The present invention relates to a method for purifying a target protein.

BACKGROUND

A recombinant gene encoding a target protein is introduced into a host such as E. coli, a yeast or a cell, whereby a recombinant protein can be expressed. As to the expressed recombinant protein, a high purity is necessary for analyzing a function and a structure, and utilizing as a preparation or the like. For the purification of the protein, various chromatographies and the like are generally used. As a method for purifying a recombinant protein, an ion-exchange chromatography is described in Mayank Saraswat, et. al. Review Article: Preparative Purification of Recombinant Proteins. Vol 2013:18, 2013.

SUMMARY OF THE INVENTION

The scope of the present invention is defined solely by the appended claims, and is not affected to any degree by the statements within this summary.

A first aspect of the present invention is a method for purifying a target protein, comprising steps of bringing a fusion protein comprising an amino acid sequence of a peptide tag, an amino acid sequence of a cleavable site of a protease and an amino acid sequence of a target protein, into contact with the protease in a solution, to cleave the peptide tag from the fusion protein, and bringing the solution comprising the peptide tag, the target protein and the protease into contact with an ion exchange resin to separate the target protein and the peptide tag, thereby obtaining a solution comprising the target protein, wherein in the fusion protein, the amino acid sequence of a cleavable site is located between the amino acid sequence of the peptide tag and the amino acid sequence of the target protein, and wherein the peptide tag is polyanionic or polycationic.

A second aspect of the present invention is a method for purifying a target protein, comprising steps of bringing a fusion protein comprising an amino acid sequence of a peptide tag, an amino acid sequence of a cleavable site of a protease and an amino acid sequence of a target protein, into contact with the protease in a solution, to cleave the peptide tag from the fusion protein, wherein the amino acid sequence of a cleavable site is located between the amino acid sequence of the peptide tag and the amino acid sequence of the target protein, and wherein the peptide tag is polyanionic or polycationic, bringing the solution comprising the peptide tag, the target protein and the protease into contact with an ion exchange resin to separate the target protein from the peptide tag and the protease, thereby the peptide tag and the protease are bound to the ion exchange resin and a flow-through fraction comprising the target protein is obtained.

A third aspect of the present invention is a method for purifying a target protein, comprising steps of preparing a sample comprising a fusion protein and contaminant proteins, wherein the fusion protein comprises an amino acid sequence of a peptide tag, an amino acid sequence of a cleavable site of a protease and an amino acid sequence of a target protein, wherein the amino acid sequence of a cleavable site is located between the amino acid sequence of the peptide tag and the amino acid sequence of the target protein, and wherein the peptide tag is polyanionic or polycationic, passing the sample through an ion exchange resin to obtain (i) the ion exchange resin to which the fusion protein is bound and (ii) a flow-through fraction comprising the contaminant proteins, removing the flow-through fraction, passing a buffer through the ion exchange resin to elute the fusion protein from the ion exchange resin to obtain a flow-through fraction comprising the fusion protein, bringing a fusion protein in the flow-through fraction into contact with the protease in a solution, to cleave the peptide tag from the fusion protein, bringing the solution comprising the peptide tag, the target protein and the protease into contact with an ion exchange resin to separate the target protein from the peptide tag and the protease, thereby the peptide tag and the protease are bound to the ion exchange resin and a flow-through fraction comprising the target protein is obtained.

BRIEF DESCRIPTION OF THE DRAWINGS

FIG. 1A shows a contaminant protein removing step, FIG. 1B shows a peptide tag cleaving step, and FIG. 1C shows a target protein acquisition step;

DETAILED DESCRIPTION OF THE PREFERRED EMBODIMENTS

Figure 1A:
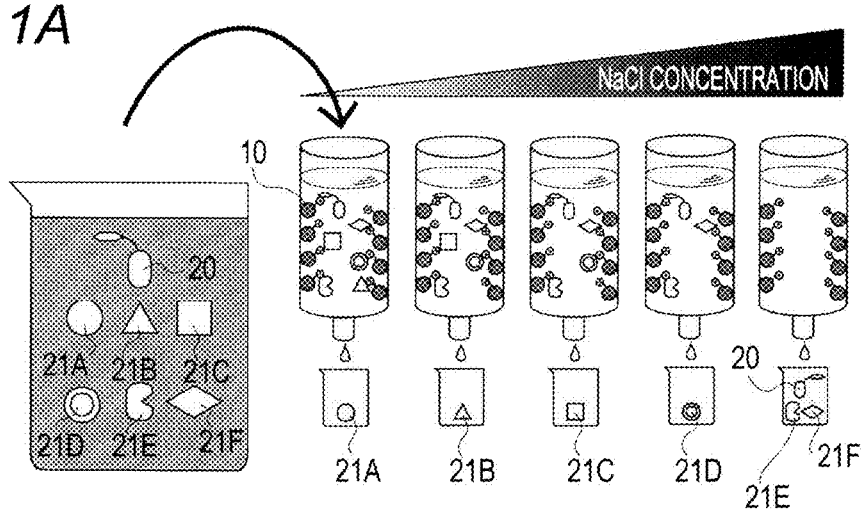
FIGS. 1A to 1C are diagrams schematically showing a principle of the purification method of the present embodiment.

The purification method of the present disclosure includes steps of cleaving a peptide tag from a fusion protein (peptide tag cleaving step), and separating a target protein and the peptide tag to acquire the target protein (target protein acquisition step).

(Peptide Tag Cleaving Step)

In the peptide tag cleaving step, a protease is brought into contact with a fusion protein containing a peptide tag and a target protein in a solution to cleave the peptide tag from the fusion protein. The fusion protein contains amino acid sequences of a peptide tag and a target protein. The peptide tag is a polyanionic peptide tag containing 2 or more acidic amino acid residues or a polycationic peptide tag containing 2 or more basic amino acid residues. When a polyanionic peptide tag is used as the peptide tag, the number of the acidic amino acid residues is preferably 12 residues or more, more preferably 18 residues or more, further preferably 24 residues or more, particularly preferably 30 residues or more, and most preferably 36 residues or more, since separation due to the ion exchange resin is improved, based on the difference in the isoelectric points between the peptide tag and the target protein. On the other hand, the upper limit of the number of the acidic amino acid residues is not particularly limited. The upper limit of the number of the acidic amino acid residues is preferably 100 residues or less, and more preferably 70 residues or less, from the viewpoint of the effect on the three-dimensional structure of the fusion protein and the like. The acidic amino acid residues contained in the polyanionic peptide tag may be either one of an aspartic acid residue and a glutamic acid residue or both of them. The polyanionic peptide tag may contain a neutral amino acid residue and/or a basic amino acid residue, other than the acidic amino acid residue. The rate of the number of the acidic amino acid residues to the number of the amino acid residues of the total peptide tags is preferably 20% or more and more preferably 60% or more, since separation from the cleaved peptide tag and the like is improved. In the sequence of the total peptide tags, the amino acid sequence containing the acidic amino acid residues may be a sequence in which all acidic amino acid residues are continuous, or one or a plurality of neutral amino acid residues and/or basic amino acid sequences may be interposed between the acidic amino acid residues. The isoelectric point of the polyanionic peptide tag is preferably 5 or less and more preferably 4 or less, since separation from the target protein is improved. The isoelectric point is a pH value when the positive and negative ion concentrations in the aqueous solution become equal to each other. The isoelectric point can be measured, for example, by isoelectric electrophoresis, or the like. Specific examples of the polyanionic peptide tag include the following peptide tags 1 to 8 (D; aspartic acid residue, E; glutamic acid residue).

<Polyanionic Peptide Tag>

```
Peptide tag 1
                                      (DE12; SEQ ID NO.: 1)
EEEEEEDDDDDD Peptide tag 2
                                      (DE18; SEQ ID NO.: 2)
EEEEEEEEEDDDDDDDDD Peptide tag 3
                                      (DE24; SEQ ID NO.: 3)
EEEEEEEEEEEEDDDDDDDDDDDD Peptide tag 4
                                      (DE30; SEQ ID NO.: 4)
EEEEEEEEEEEEEEEDDDDDDDDDDDDDDD Peptide tag 5
                                      (DE36; SEQ ID NO.: 5)
EEEEEEEEEEEEEEEEEEDDDDDDDDDDDDDDDDDD Peptide tag 6
                                      (DED; SEQ ID NO.: 6)
NVEGKTGNATDEEEEEEEEEEEDDDDDDDDDDDDEDSGAEIQDDDE

EGFDDEEEFDDDDDDEH

DDDDLENEENELEELEERVEARKK

Peptide tag 7
                                      (DES; SEQ ID NO.: 7)
DLSNVEGKTGNATDEEEEEEEEEEEEDDDDDDDDDDDDEDSGAE Peptide tag 8
                                      (EO24; SEQ ID NO.: 8)
EEEEEEEEEEEEEEEEEEEEEEEE
```

When a polycationic peptide tag is used as the peptide tag, the number of the basic amino acid residues is preferably 12 residues or more, more preferably 18 residues or more, and further preferably 24 residues or more, since separation due to the ion exchange resin is improved, based on the difference in the isoelectric points between the peptide tag and the target protein. On the other hand, the upper limit of the number of the basic amino acid residues is not particularly limited. The upper limit of the number of the acidic amino acid residues is preferably 100 residues or less, and more preferably 70 residues or less, from the viewpoint of the effect on the three-dimensional structure of the fusion protein and the like. The basic amino acid residues contained in the polycationic peptide tag is one or two or more kinds selected from a group consisting of an arginic acid residue, a histidine residue and a lysine residue. The polycationic peptide tag may contain a neutral amino acid residue and/or an acidic amino acid residue, other than the basic amino acid residue. The rate of the number of the basic amino acid residues to the number of the amino acid residues of the total peptide tags is preferably 20% or more and more preferably 60% or more, since separation from the cleaved peptide tag and the like is improved. In the sequence of the total peptide tags, the amino acid sequence containing the basic amino acid residues may be a sequence in which all basic amino acid residues are continuous, or one or a plurality of neutral amino acid residues and/or acidic amino acid sequences may be interposed between the basic amino acid residues. The isoelectric point of the polycationic peptide tag is preferably 10 or more and more preferably 11 or more, since separation from the target protein is improved.

The target protein is not particularly limited. Examples of the target protein include proteins such as enzymes, receptors, interferons, interleukins, antibodies, and fluorescent proteins. The isoelectric point of the target protein is not particularly limited. When the peptide tag is polyanionic, the isoelectric point is preferably 5 or more and more preferably 6 or more, since separation from the peptide tag and the like is improved. On the other hand, when the peptide tag is polycationic, the isoelectric point is preferably 8 or less and more preferably 7 or less.

In the fusion protein, the peptide tag may be bound to either N-terminal side or C-terminal side of the target protein. An amino acid sequence of a cleavable site to be recognized by a protease is inserted between the target protein and the peptide tag. The cleavable site to be recognized by a protease is not particularly limited. Examples include recognition sequences of a protease such as HRV3C, PreScission protease, factor Xa, thrombin, or TEV protease. The protease is brought into contact with the fusion protein in a solution, whereby the peptide tag can be cleaved from the fusion protein. The reaction temperature and the reaction time can be properly set according to the kind of the protease and the like. The isoelectric point of the fusion protein is not particularly limited. When the peptide tag is polyanionic, the isoelectric point is preferably less than 6 and more preferably less than 5, since separation from the target protein is improved. On the other hand, when the peptide tag is polycationic, the isoelectric point is preferably 9 or more and more preferably 10 or more.

(Target Protein Acquisition Step)

In the target protein acquisition step, the sample solution treated with the protease is brought into contact with an ion exchange resin, and the target protein and the peptide tag are separated to acquire a solution containing the target protein. In the solution after the protease reaction, the cleaved peptide tag, the target protein and the protease are contained. The difference in the isoelectric points is caused between the target protein and the peptide tag when the peptide tag is cleaved from the fusion protein, thus the solution after the protease reaction is brought into contact with an ion exchange resin, thereby separating the fusion protein and the peptide tag based on the difference in the isoelectric points. In a case where the peptide tag is polyanionic, an anion exchange resin is preferably used as the ion exchange resin. When a solution containing the polyanionic peptide tag, the target protein and the protease after reaction by the protease is passed through an anion exchange resin, the polyanionic peptide tag binds to the anion exchange resin, and the target protein passes without binding to the ion exchange resin. A solution containing the target protein can be acquired by collecting this flow-through fraction. The ion exchange group of the anion exchange resin is not particularly limited, and a quaternary ammonium (QA), a quaternary aminoethyl (QAE), diethylaminoethyl (DEAE) and the like can be used. Specific examples include Hitrap HP Q (GE Healthcare), TOYOPEARL GigaCap Q-650M, TOYOPEARL Q-600C AR, TOYOPEARL QAE-550, TOYOPEARL DEAE-650M, TOYOPEARL SuperQ-650M (all, Tosoh Corporation), Q101, DE101 (Mitsubishi Chemical Corporation), and the like. As a carrier of the ion exchange group, cellulose, dextran, agarose, a hydrophilic vinyl polymer or the like can be used. The salt concentration of the solution containing the polyanionic peptide tag, the target protein and the protease is preferably 500 mM or less and more preferably 250 mM or less, since separation from the polyanionic peptide tag is improved. The pH of the solution is preferably 5 or more and 9 or less, and more preferably 6 or more and 8 or less. As a buffer used for adjustments of the salt concentration and pH of the solution, a phosphate buffer, a citrate buffer, an acetate buffer, a tris buffer, a MOPS buffer, a HEPES buffer or the like can be used. These buffers contain a salt with a weak acid or weak base used for obtaining a buffer action. In addition, salts such as sodium chloride, potassium chloride and calcium chloride can be used. The salt concentration of a buffer, a sample solution or the like herein means a concentration of a salt other than the salt intended for the buffer action described above.

In a case where the peptide tag is polycationic, a cation exchange resin is preferably used. As the polyanionic peptide tag, when a solution containing the polycationic peptide tag, the target protein and the protease after reaction by the protease is passed through a cation exchange resin, the polycationic peptide tag binds to the cation exchange resin, and the target protein passes without binding to the cation exchange resin, thus a solution containing the target protein can be acquired by collecting this follow-through fraction. The ion exchange group of the cation exchange resin is not particularly limited, and sulfopropyl (SP), carboxymethyl (CM), and the like can be used. Specific examples include SP Sepharose, CM Sepharose (both, GE Healthcare), SP-5PW, SP-NPR, CM-5PW, CM-STAT (all, Tosoh Corporation), and the like. As a carrier of the ion exchange group, cellulose, dextran, agarose, a hydrophilic vinyl polymer or the like can be used. The salt concentration of the solution containing the polycationic peptide tag, the target protein and the protease is preferably 500 mM or less and more preferably 250 mM or less, since separation from the polycationic peptide tag is improved. The pH of the solution is preferably 5 or more and 9 or less, and more preferably 6 or more and 8 or less.

The isoelectric point of the protease is preferably different from the isoelectric point of the target protein. This makes it possible to easily separate the target protein and the protease, after cleaving the peptide tag with the protease. The protease may be fused with a peptide tag. This makes it possible to adjust the isoelectric point of the protease to a desired value. As the peptide tag fused to the protease, the same one as the peptide tag to be bound to the fusion protein described above can be used. The amino acid sequence of the peptide tag to be bound to the protease may be the same as or different from the amino acid sequence of the peptide tag to be bound to the fusion protein. In a case where the peptide tag to be bound to the fusion protein is polyanionic, a peptide tag of the protease is also preferably polyanionic, and in a case where the peptide tag to be bound to the fusion protein is polycationic, a polycationic peptide tag is preferably also bound to the protease, since the cleaved peptide tag and the protease can be separated by the ion exchange resin at the same time. The amino acid sequence of the peptide tag to be bound to the protease is more preferably the same as the amino acid sequence of the peptide tag contained in the fusion protein. Thereby, the protease has an isoelectric point different from that of the target protein and also different from that of the target protein. The protease fused with the peptide tag preferably does not have a cleavable site to be recognized by this protease, in order to avoid decomposition by itself. When the protease fused with the peptide tag is used, the cleaved peptide tag, the target protein and the protease fused with the peptide tag are contained in the solution after the protease reaction. This solution is passed through an ion exchange resin, the protease fused with the peptide tag also binds to the ion exchange resin, together with the cleaved peptide tag. On the other hand, the target protein passes without binding to the ion exchange resin. Therefore, high purity target protein can be acquired without separately going through a step of separating the protease.

In the present embodiment, a step of expressing the fusion protein and a step of removing contaminant proteins may be contained, before the peptide tag cleaving step.

(Expression Step)

The fusion protein can be acquired by introducing a polynucleotide containing a base sequence encoding a peptide tag and a base sequence encoding a target protein into a vector, then introducing the vector into a host cell and expressing the fusion protein in the host cell, according to a known recombinant protein expression method. A polynucleotide encoding a peptide tag and a polynucleotide encoding a target protein can be acquired by a known method such as chemical synthesis. The acquired polynucleotides can be amplified according to a known gene amplification method using these as templates. The amplified polynucleotide and an expression vector are treated with a restriction enzyme, and bound using an appropriate DNA ligase, whereby a recombinant expression vector containing the polynucleotides each encoding a peptide tag and a target protein can be constructed. In the construction of the expression vector, the polynucleotide encoding a peptide tag may be arranged at the 5' side or 3' side of the polynucleotide encoding a target protein. Between the base sequence encoding a peptide tag and the base sequence encoding a target protein, a base sequence encoding a cleavable site recognized by a protease is inserted. The host is not particularly limited. As the host, $E.$ $coli$, a yeast, an insect cell, an insect body, an animal cell, a plant cell or the like can be used. The expression vector is not particularly limited. The expression vector includes plasmid vectors, pharge vectors, virus vectors and the like. The expression vector can be properly selected depending on the used host. The expression vector may contain a regulatory sequence such as a replication origin, a promoter sequence or an enhancer sequence, or a sequence such as a selectable marker. Introduction of an expression vector into a host can be performed according to a known method depending on the host. Examples of the method include a calcium phosphate method, an electroporation method, a lipofection method, and the like. As described above, a transformant in which the expression vector is introduced into the host cell can be obtained. The obtained transformant is incubated under preferred conditions, thus a fusion protein can be produced.

After expressing the fusion protein, a treatment such as extraction, crushing, centrifugation, solubilization and body fluid collection is performed on cells of the host, tissue, insect body, and the like, as necessary, to acquire a sample solution as a cell culture liquid, an extract, a homogenate, a solution, a body fluid, or the like. For the preparation of the sample solution, a buffer such as a phosphate buffer, a citrate buffer, an acetate buffer, a tris buffer, a MOPS buffer or a HEPES buffer can be used. These buffers contain a salt with a weak acid or weak base used for obtaining a buffer action. In addition, salts such as sodium chloride, potassium chloride and calcium chloride can be used. The salt concentration of the buffer herein means a concentration of a salt other than the salt intended for the buffer action described above. The salt concentration of the buffer is preferably 50 mM or more and 500 mM or less, and more preferably 50 mM or more and 250 mM or less, from the viewpoint of stability of the fusion protein, easiness of adjustment in the separation step, and the like. The pH of the buffer is preferably 5 or more and 9 or less, and more preferably 6 or more and 8 or less, from the viewpoint of stability of the fusion protein, easiness of adjustment in the separation step, and the like.

When a sample is acquired using an $Escherichia$ $coli$ expression system, a plasmid vector can be used as an expression vector. Specific examples of the plasmid vector include pET, pGEX, pCold, pMAL, pCAL, and the like. The expression vector may contain a promoter sequence such as a replication origin, lac, T7 or tac, an enhancer sequence, or a sequence of a selectable marker such as ampicillin resistance gene, kanamycin resistance gene, or tetracycline resistance gene. Introduction of an expression vector into $E.$ $coli$ can be performed by a calcium phosphate method, an electroporation method, a lipofection method, and the like. After the introduction of an expression vector, $E.$ $coli$ is cultured in a medium containing the selectable marker, whereby a transformant in which the expression vector is introduced into $E.$ $coli$ can be selected. The thus-obtained transformant is proliferated under preferred conditions. Then, the proliferated transformant is expressed and induced depending on the selected promoter to produce a fusion protein. After expressing the fusion protein, a sample solution containing the fusion protein and contaminant proteins derived from $E.$ $coli$ can be acquired by crushing $E.$ $coli$ or the like.

When using an insect body such as silkworm or insect cells as an expression system, a transfer vector can be used. The transfer vector is transduced into the insect cells together with baculovirus DNA, and then an objective gene can be inserted into the baculovirus DNA by homologous recombination. Specific examples of the transfer vector include pM01, pM02, pHS01, pHS02, and the like. The transfer vector preferably contains a promoter such as a polyhedrin promoter or a p10 promoter. Examples of the insect cells include Sf9, Sf21, High5, TN-368, Bm5, and the like. Examples of the baculovirus include nuclear polyhedrosis virus (NPV), and specifically, AcMNPV, BmNPV and the like can be exemplified. The transfer vector and linearized baculovirus DNA are introduced into the insect cells, whereby homologous recombination occurs, and a recombinant baculovirus into which an objective gene is inserted is obtained. A virus solution containing a recombinant baculovirus is inoculated into an insect body or insect cells, or the like, whereby the recombinant baculovirus can be infected. The insect body such as silkworm may be in any form of imago, pupa, and larva. The insect body or insect cells are infected with the recombinant baculovirus, and bred or cultured for 1 to 7 days, whereby a fusion protein can be expressed. After expressing the fusion protein, a sample solution containing the fusion protein and contaminant proteins derived from the insect body or insect cells can be acquired by crushing the insect body or insect cells, or the like.

The protease can be also expressed by a known expression system in the same manner. The protease fused with the peptide tag can be obtained by using the protease as the target protein, in the expression of the fusion protein described above. The fusion protein and the protease can be expressed by introducing a vector into which a polynucleotide containing a base sequence encoding both amino acid sequences into a host. A vector into which a polynucleotide encoding the fusion protein is introduced and a vector into which a polynucleotide encoding the protease is inserted may be introduced into the host to express the fusion protein and the protease. The vector into which a polynucleotide encoding the fusion protein is inserted is introduced into the host, and the vector into which a polynucleotide encoding the protease is inserted is introduced into the host, and the fusion protein and the protease are expressed alone respectively, and then may be mixed. In this case, the hosts may be the same kind or the different kind, and are preferably the same kind, in the aspect of easiness of handling after expression and the like.

Examples of the fusion protein include the following constructs 1 to 12 obtained by fusing NAD(P)H dehydrogenase, quinone 1 human (NQO1; pI=8.91; SEQ ID NO.: 9) or Luciferase (pI=6.71; SEQ ID NO.: 10) that is a target protein and the above peptide tags 1 to 8, and inserting a cleavable site recognized by protease HRV3C therebetween. Examples of the protease fused with the peptide tag include the following construct 13 obtained by fusing HRV3C (pI=8.46; SEQ ID NO.: 11) that is a protease and the above peptide tag 7.

Construct 1 DE12-HRV3Csite-NQO1 (SEQ ID NO.: 12)
Construct 2 DE18-HRV3Csite-NQO1 (SEQ ID NO.: 13)
Construct 3 DE24-HRV3Csite-NQO1 (SEQ ID NO.: 14)
Construct 4 DE30-HRV3Csite-NQO1 (SEQ ID NO.: 15)
Construct 5 DE36-HRV3Csite-NQO1 (SEQ ID NO.: 16)
Construct 6 DED-HRV3Csite-NQO1 (SEQ ID NO.: 17)
Construct 7 DES-HRV3Csite-NQO1 (SEQ ID NO.: 18)
Construct 8 EO24-HRV3Csite-NQO1 (SEQ ID NO.: 19)
Construct 9 NQO1-HRV3Csite-DED (SEQ ID NO.: 20)
Construct 10 NQO1-HRV3Csite-DES (SEQ ID NO.: 21)
Construct 11 DED-HRV3Csite-Luciferase (SEQ ID NO.: 22)
Construct 12 DES-HRV3Csite-Luciferase (SEQ ID NO.: 23)
Construct 13 DED-HRV3C (SEQ ID NO.: 24)

(Contaminant Protein Removing Step)

The sample solution containing the fusion protein expressed as described above contains contaminant proteins such as host-derived endogenous proteins. Therefore, a step of separating the fusion protein and the contaminant proteins, and removing the contaminant proteins may be included, before the target protein acquisition step. The phrase "separating the fusion protein and the contaminant proteins" includes extracting and purifying the fusion protein, and storing into a container different from the contaminant proteins. The contaminant proteins may be substantially completely separated, or a part of the contaminant proteins may be separated. A part or all of the contaminant proteins is separated, whereby the purity of the fusion protein can be improved. The contaminant protein means a protein such as host-derived endogenous proteins, other than the fusion protein and the target protein. A peptide tag is fused to the target protein, whereby the fusion protein has a different isoelectric point, to an extent that it can be sufficiently separated from the contaminant proteins. As described above, in a case where the peptide tag is polyanionic, the isoelectric point of the fusion protein is preferably less than 6 and more preferably less than 5, and in a case where the peptide tag is polycationic, the isoelectric point of the fusion protein is preferably 9 or more and more preferably 10 or more. The isoelectric point of many proteins is generally 6 to 7, thus when the isoelectric point of the fusion protein is in the above range, separation of the fusion protein from the contaminant proteins becomes easier, and purity of the fusion protein can be improved.

The separation means is not particularly limited, and a known separation means can be used. Separation by an ion exchange resin is preferred, since good separation from the contaminant proteins is obtained. In a case where the peptide tag is polyanionic, separation by an anion exchange resin is more preferred. The ion exchange group of the anion exchange resin is not particularly limited, and a quaternary ammonium (QA), a quaternary aminoethyl (QAE), diethylaminoethyl (DEAE) and the like can be used. Specific examples include Hitrap HP Q (GE Healthcare), TOYOPEARL GigaCap Q-650M, TOYOPEARL Q-600C AR, TOYOPEARL QAE-550, TOYOPEARL DEAE-650M, TOYOPEARL SuperQ-650M (all, Tosoh Corporation), Q101, DE101 (Mitsubishi Chemical Corporation), and the like. As a carrier of the ion exchange group, cellulose, dextran, agarose, a hydrophilic vinyl polymer or the like can be used. The sample solution containing the fusion protein and the contaminant proteins is passed through an anion exchange resin, thereby binding the fusion protein to the anion exchange resin. Thereafter, for example, the salt concentration of an eluate is increased to elute the contaminant proteins, then the fusion protein is eluted from the ion exchange resin with the eluate with a high salt concentration, whereby the fusion protein can be purified. Examples of a method for increasing the salt concentration of an eluate include a stepwise method in which the salt concentration is stepwisely changed to elute an objective protein, a gradient method in which the salt concentration is continuously changed to elute an objective protein. As the buffer, a buffer such as a phosphate buffer, a citrate buffer, an acetate buffer, a tris buffer, a MOPS buffer or a HEPES buffer can be used. The salt concentration of the buffer is preferably set in the range of 50 mM or more and 2000 mM or less, and more preferably in the range of 50 mM or more and 1000 mM or less, from the viewpoint of separation from the contaminant proteins, stability of the fusion protein, and the like. Particularly, when the salt concentration of the buffer is set at 600 mM or more and more preferably 750 mM or more, separation from the contaminant proteins is improved. The range of pH of the buffer is not particularly limited. The range of pH of the buffer is preferably in the range of 5 or more and 9 or less, and more preferably in the range of 6 or more and 8 or less, from the viewpoint of separation from the contaminant proteins, stability of the fusion protein, and the like.

In a case where the peptide tag is polycationic, a cation exchange resin is preferably used. The ion exchange group of the cation exchange resin is not particularly limited, and sulfopropyl (SP), carboxymethyl (CM), and the like can be used. Specific examples include SP Sepharose, CM Sepharose (both, GE Healthcare), SP-5PW, SP-NPR, CM-5PW, CM-STAT (all, Tosoh Corporation), and the like. As a carrier of the ion exchange group, cellulose, dextran, agarose, a hydrophilic vinyl polymer or the like can be used. As in the case of using an anion exchange resin, the salt concentration of the eluate is increased, whereby the fusion protein can be purified. The salt concentration of the buffer is preferably set in the range of 50 mM or more and 2000 mM or less, and more preferably in the range of 50 mM or more and 1000 mM or less, from the viewpoint of separation from the contaminant proteins, stability of the fusion protein, and the like. The range of pH of the buffer is not particularly limited. The range of pH of the buffer is preferably in the range of 5 or more and 9 or less, and more preferably in the range of 6 or more and 8 or less, from the viewpoint of separation from the contaminant proteins, stability of the fusion protein, and the like.

Figure 1B:
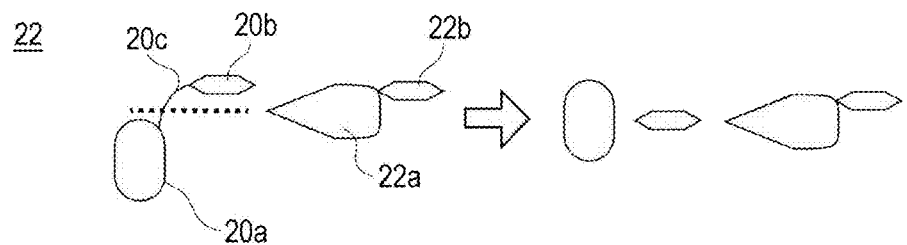
Figure 1C:
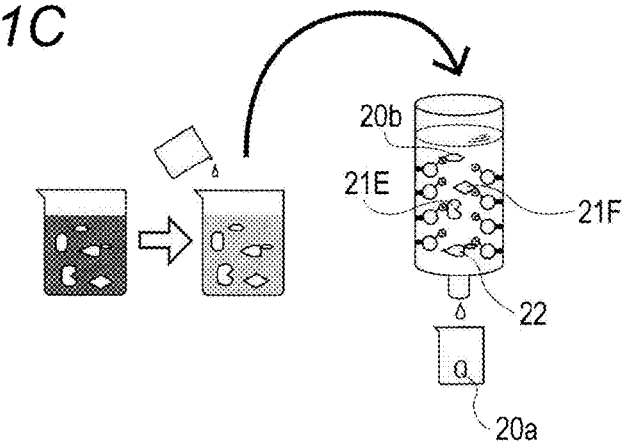

FIGS. 1A to 1C are schematic diagrams showing one embodiment, FIG. 1A shows a contaminant protein removing step, FIG. 1B shows a peptide tag cleaving step, and FIG. 1C shows a target protein acquisition step. The principle of the purification method of the present embodiment will be described based on this diagram. When a fusion protein is expressed in a host cell, a sample solution such as a disrupted cell suspension contains contaminant proteins 21A to 21F such as host-derived endogenous proteins, other than a fusion protein 20. The isoelectric points of the contaminant proteins 21 are high in the order of A to F. In this present embodiment, a polyanionic peptide tag 20b is bound to a target protein 20a, thereby lowering the isoelectric point of the fusion protein 20. The fusion protein 20 in which the isoelectric point is lowered can be held in an anion exchange resin 10 up to a high salt concentration. On the other hand, most of host-derived contaminant proteins cannot be held in the anion exchange resin 10 up to the same salt concentration. The fusion protein and the contaminant proteins are separated, based on the difference in the isoelectric points. Specifically, when a sample is brought into contact with the anion exchange resin 10, the contaminant protein 21A with a high isoelectric point passes without binding to the anion exchange resin. Other contaminant proteins and the fusion protein 20 bind to the anion exchange resin 10. When the salt concentration of the eluate is increased, contaminant proteins are eluted in the higher order of the isoelectric point (21B to 21D). The fusion protein 20 is eluted by an eluate with further higher salt concentration. This elution fraction contains contaminant proteins 21E and 21F with an isoelectric point close to that of the fusion protein 20. The salt concentration of the eluate is adjusted as described above, whereby many contaminant proteins can be separated, thus a high purity fusion protein can be obtained. The difference in the isoelectric points between the fusion protein and the contaminant proteins is relatively large, thus good separation is obtained also by a stepwise method in which the salt concentration is stepwisely changed to elute a protein (FIG. 1A).

The fusion protein 20 contains a cleavable site 20c to be recognized by the protease 22, between the target protein 20a and the peptide tag 20b. In a protease 22 fused with the peptide tag, a peptide tag 22b is bound to a protease 22. When the fusion protein 20 and the protease 22 are reacted in the solution, the peptide tag 20b is cleaved from the fusion protein 20 (FIG. 1B). The target protein 20a, the cleaved peptide tag 20b, the protease 22 fused with the peptide tag and contaminant proteins 21E and 21F remained in the contaminant protein removing step are contained in the solution after reaction. A peptide tag 20b with a low isoelectric point is cleaved, thus the isoelectric point of the target protein 20a becomes high as compared to that of the fusion protein 20. The contaminant proteins 21E and 21F have an isoelectric point relatively close to that of the fusion protein 20, thus the target protein 20a has an isoelectric point higher than those of those proteins. Furthermore, the target protein 20a has an isoelectric point higher than those of the cleaved peptide tag 20b and the protease 22 fused with the peptide tag 22b. Therefore, when this solution is diluted to lower the salt concentration and passed through the anion exchange resin 10, the cleaved peptide tag 20b, the protease fused 22 with the peptide tag and contaminant proteins 21E and 21F bind to the anion exchange resin 10, but the target protein 20a passes without binding thereto. High purity target protein 20a can be acquired by collecting this flow-through fraction (FIG. 1C).

EXAMPLES

Hereinbelow, the present invention will be further described in detail with reference to examples, but the present invention is not limited to these examples.

Example 1 [Expression and Purification of Fusion Protein DE12-HRV3Csite-NQO1 (Construct 1; pI=5.84)]

Peptide tag 1 (DE12) was fused to the N-terminal side of NAD(P)H dehydrogenase, quinone 1 human (NQO1; pI=8.91) that is a target protein, and expression and purification of a fusion protein containing a cleavable site HRV3Csite recognized by protease HRV3C between NQO1 and DE12 were performed.

(1) Construction of pM01_DE12 Vector

A pM01_DE12 vector in which the peptide tag DE12 was inserted into a pM01 vector was constructed.

Polynucleotides encoding DE12 (SEQ ID NOs.: 25 and 26) were annealed in pairs to prepare an insert part. A NheI site of the pM01 vector (SYSMEX CORPORATION) was treated with NheI (TAKARA BIO INC.), and the insert part was inserted using In-Fusion HD Cloning Kit (Clontech Laboratories, Inc.). Stellar Competent Cells were transformed with the constructed vector, then the obtained transformant was seeded on a LBA plate, and cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primer 1 (SEQ ID NO.: 27) and primer 2 (SEQ ID NO.: 28) for sequence confirmation, then the base sequence was analyzed by a DNA sequencer (Thermo Fisher Scientific Inc.). A vector into which the insert part was introduced, that had no variation in other part, was defined as pM01_DE12.

(2) Construction of pM01_DE12_HRV3Csite_NQO1

An expression vector pM01_DE12_HRV3Csite_NQO1 into which a polynucleotide (SEQ ID NO.: 29) encoding NQO1 (SEQ ID NO.: 9) was inserted into pM01_DE12 was constructed.

The polynucleotide encoding NQO1 and primers 3F (SEQ ID NO.: 30) and 3R (SEQ ID NO.: 31) corresponding to the insert part were prepared, and the insert part was amplified using KOD-Plus- (TOYOBO CO., LTD.) as a PCR enzyme, under the following PCR conditions. The amplified PCR product was migrated by 1.0% (w/v) agarose electrophoresis, and the part matched to the length of the insert part was cut out from the gel and purified to prepare an insert part. A SmaI site of the pM01_DE12 vector was treated with SmaI (TAKARA BIO INC.), and the insert part was inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pM01_DE12_HRV3Csite_NQO1.
<PCR Conditions>
Reaction 1: 94.0° C., 2 minutes; Reaction 2: 94.0° C., 15 seconds; Reaction 3: 52.0° C., 30 seconds; Reaction 4: 68.0° C., 1 minute per 1 kbp; Reaction 5: Reaction 2 to Reaction 4 are repeated 30 times (3) Preparation of Recombinant Baculovirus and Expression of Fusion Protein DE12-HRV3Csite-NQO1 pM01_DE12_HRV3Csite_NQO1 and baculovirus DNA were introduced into silkworm culture cells (BmN cells), and homologous recombination of virus was performed. The culture cells were cultured for 6 days, and the recombinant virus was collected. Thereafter, a virus solution diluted 50 times with MilliQ water was inoculated into pupa of silkworm, and the pupa was incubated for 6 days.

(4) Purification of DE12-HRV3Csite-NQO1

After incubation, the pupa of silkworm was collected, and 50 mL of a buffer (20 mM Tris-HCl (pH 8.0), 150 mM NaCl, 1 tablet Complete EDTA free (Roche), phenylthiourea) was added per a pupa to homogenate the pupa. The solution was centrifuged (8,000 g, 10 minutes), then the supernatant fraction was filtered with 0.8 uM of a filter agent, and the filtrate was collected. The collected filtrate was loaded on an ion exchange resin (Hitrap Q HP (1 mL)), and purified using a mixed solution of 20 mM Tris-HCl (pH 8.0, 150 mM NaCl; buffer A) and 20 mM Tris-HCl (pH 8.0, 1000 mM NaCl; buffer B). First, only buffer A (NaCl concentration of 150 mM) was flown through the ion exchange resin (EL0), and a fraction eluted with a 3:1 mixed solution of buffer A:buffer B (NaCl concentration of 363 mM) (EL1), a fraction eluted with a 1:1 mixed solution of buffer A:buffer B (NaCl concentration of 575 mM) (EL2), a fraction eluted with a 1:3 mixed solution of buffer A:buffer B (NaCl concentration of 788 mM) (EL3), and finally, a fraction eluted with only buffer B (NaCl concentration of 1000 mM) (EL4) were each collected.

(5) Detection of DE12-HRV3Csite-NQO1

SDS (Sodium dodecyl sulfate)-polyacrylamide gel electrophoresis (SDS-PAGE) was performed using 5 to 20% gradient gel and an electrophoresis apparatus (APRO Science Inc.). A sample and β-ME Sample Treatment for Tris SDS (COSMO BIO Co., Ltd.) were mixed in a volume ratio of 1:1, and treated at 100° C. for 3 minutes, then 5 uL of the resulting solution was loaded on the gel. As a molecular weight marker, 2.5 uL of Blue Star (NIPPON Genetics Co, Ltd.) was loaded on the gel. The gel loaded with the sample was migrated at a voltage of 400 V for 14 minutes, and then transferred to a membrane using Trans-Blot Turbo Transfer System (Bio-Rad Laboratories, Inc.). The transferred membrane was set in i-Bind system (Thermo Fisher Scientific Inc.), and an antigen-antibody reaction was performed. In the antigen-antibody reaction, an ANTI-FLAG (registered trademark) M2-Peroxidase (HRP) antibody (Merck & Co., Inc.) or an Anti-NQO1 antibody (Cell Signaling Technology, Inc.) and Anti-IgG (H+L chain) (Mouse) pAb-HRP (Beckman Coulter, Inc.) were diluted 2000 times and used. Also, Luminata Forte (Merck & Co., Inc.) as a HRP reagent for detection and Gel Doc XR+ system (Bio-Rad Laboratories, Inc.) as a detector were used.

Figure 2:
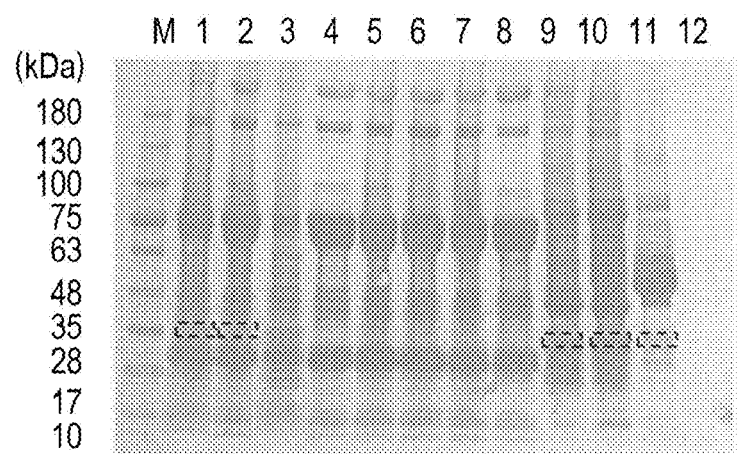
FIG. 2 is a figure showing the results of SDS (Sodium dodecyl sulfate)-polyacrylamide gel electrophoresis (SDS-PAGE) in Example 1.
Figure 3:
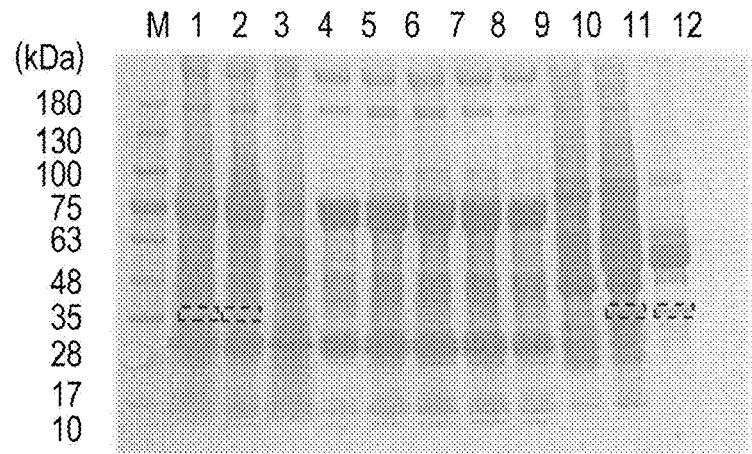
FIG. 3 is a figure showing the results of SDS-PAGE in Example 2.
Figure 4:
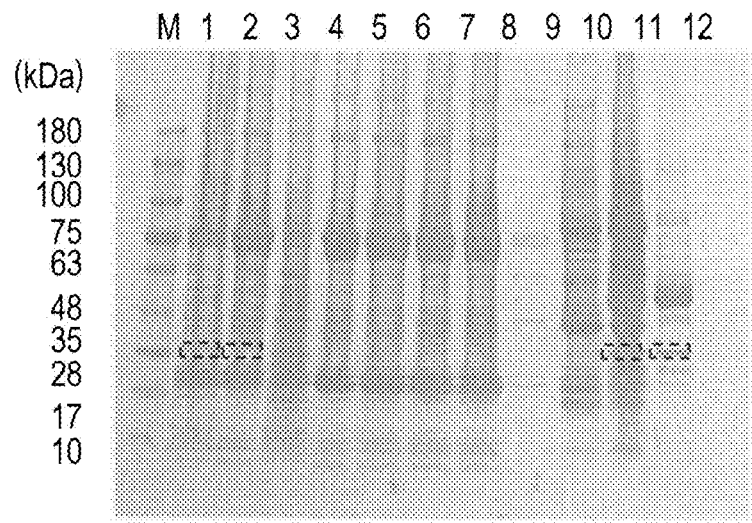
FIG. 4 is a figure showing the results of SDS-PAGE in Example 3.
Figure 5:
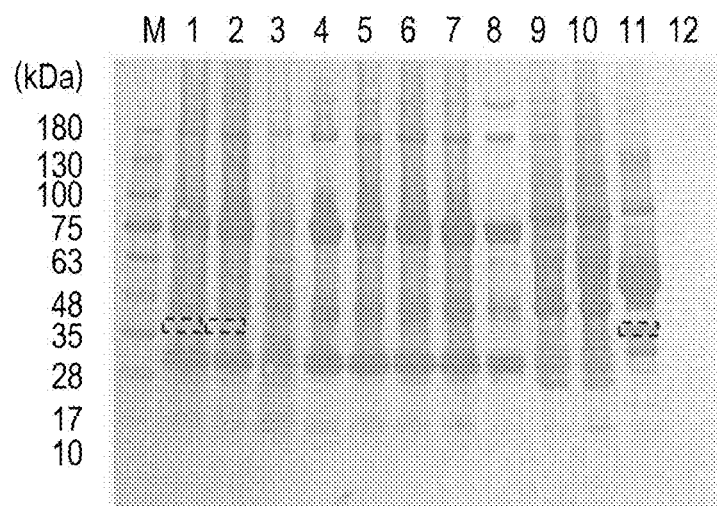
FIG. 5 is a figure showing the results of SDS-PAGE in Example 4.
Figure 6:
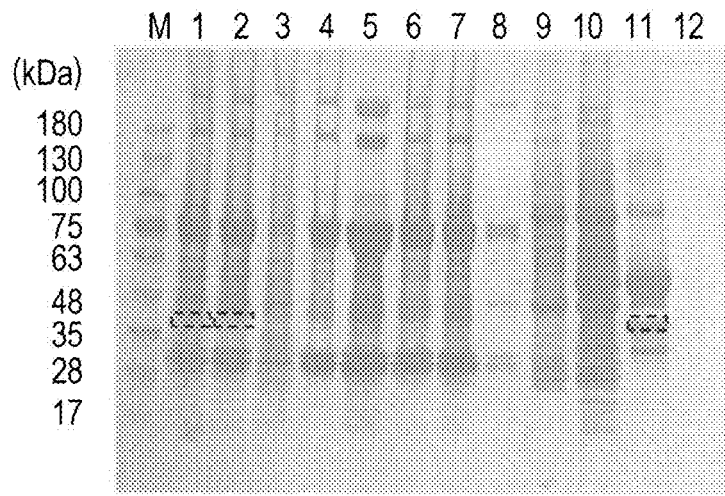
FIG. 6 is a figure showing the results of SDS-PAGE in Example 5.
Figure 7:
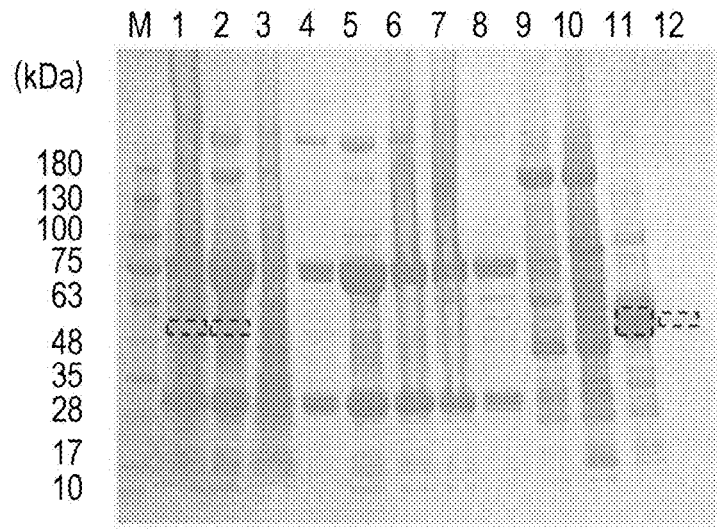
FIG. 7 is a figure showing the results of SDS-PAGE in Example 6.
Figure 8:
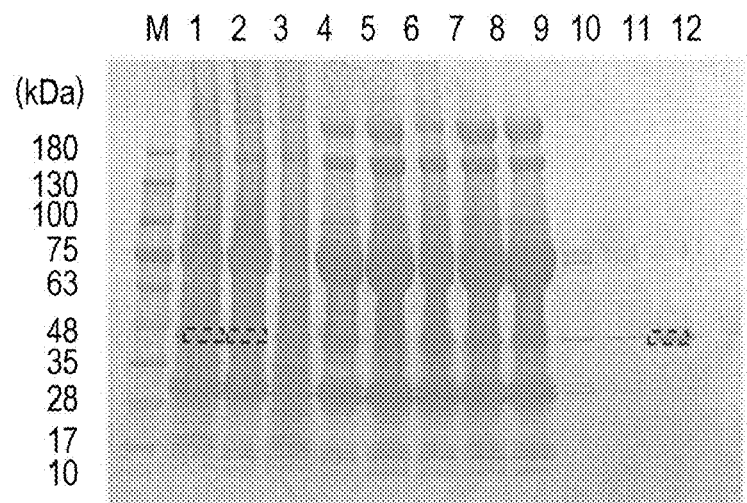
FIG. 8 is a figure showing the results of SDS-PAGE in Example 7.
Figure 9:
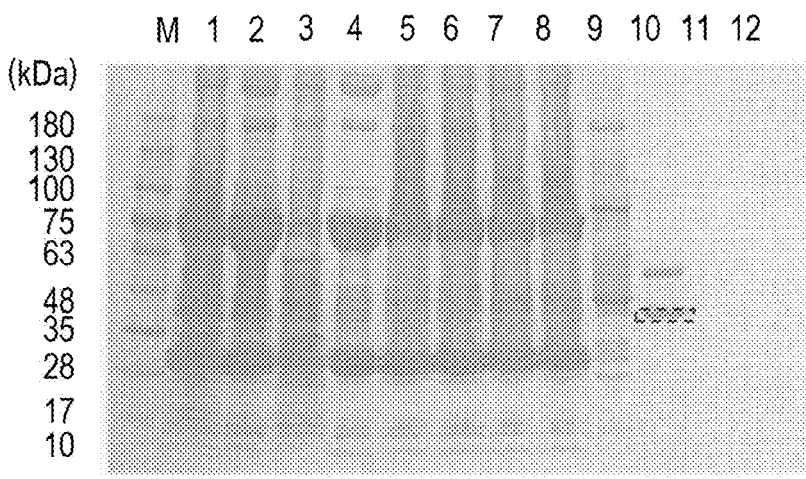
FIG. 9 is a figure showing the results of SDS-PAGE in Example 8.
Figure 10:
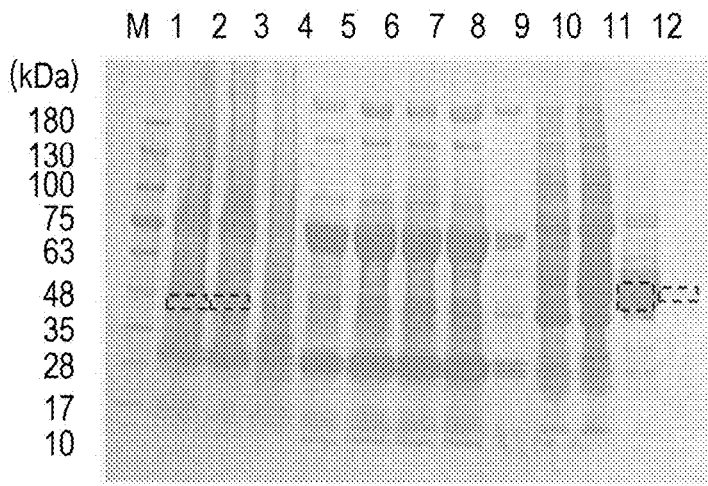
FIG. 10 is a figure showing the results of SDS-PAGE in Example 9.
Figure 11:
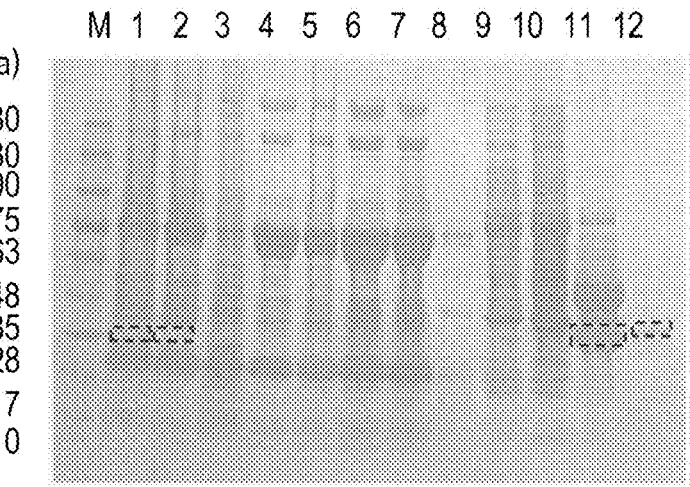
FIG. 11 is a figure showing the results of SDS-PAGE in Example 10.
Figure 12:
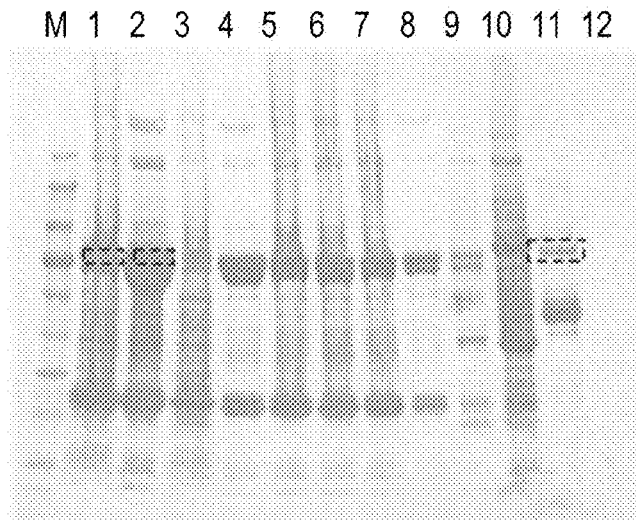
FIG. 12 is a figure showing the results of SDS-PAGE in Example 11.
Figure 13:
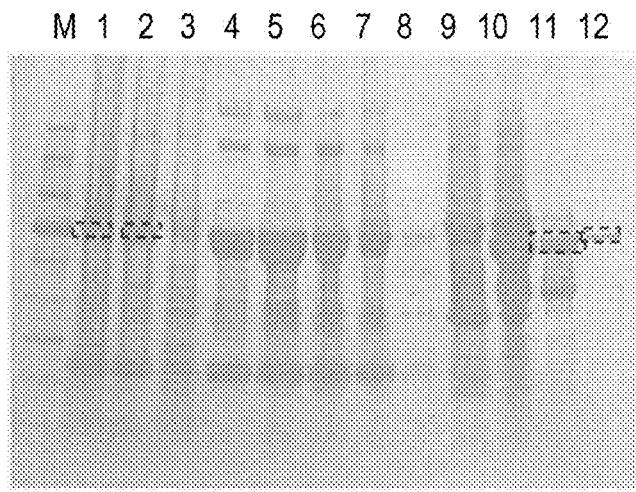
FIG. 13 is a figure showing the results of SDS-PAGE in Example 12.

After performing western blotting, the used membrane was stained by GelCode Blue Stain Reagent (Thermo Fisher Scientific Inc.), and excess staining was bleached, then the image was photographed using Gel Doc XR+ system (Bio-Rad Laboratories, Inc.). The results were shown in FIG. 2. In FIG. 2, the results of electrophoresis are shown as follows; M: molecular weight marker, lane 1: homogenate solution, lane 2: supernatant fraction after centrifugation, lane 3: precipitated fraction after centrifugation, lanes 4 to 7: flow-through fractions 1 to 4 of the ion exchange resin, lane 8: elution fraction by buffer A (NaCl concentration of 150 mM) (EL0), lane 9: elution fraction by a 3:1 mixed solution of buffer A:buffer B (NaCl concentration of 363 mM) (EL1), lane 10: elution fraction by a 1:1 mixed solution of buffer A:buffer B (NaCl concentration of 575 mM) (EL2), lane 11: elution fraction by a 1:3 mixed solution of buffer A:buffer B (NaCl concentration of 788 mM) (EL3), and lane 12: elution fraction by buffer B (NaCl concentration of 1000 mM) (EL4). The part surrounded by a broken line shows a band containing the target protein. Explanation of each lane is common in FIGS. 3 to 15.

Example 2 [Expression and Purification of Fusion Protein DE18-HRV3Csite-NQO1 (Construct 2; pI=5.03)]

Peptide tag 2 (DE18) was fused to the N-terminal side of NQO1 that is a target protein, and expression and purification of a fusion protein containing HRV3Csite between NQO1 and DE18 were performed.

The same procedures were carried out as in Example 1, except for preparing an insert part using polynucleotides (SEQ ID NOs.: 32 and 33) encoding DE18 (SEQ ID NO.: 2) in place of the polynucleotides encoding the peptide tag DE12, to construct a pM01_DE18 vector.

Further, pM01_DE18 HRV3Csite_NQO1 was constructed, and a recombinant baculovirus was prepared in the same manner as in Example 1, then expression, purification and detection of fusion protein DE18-HRV3Csite-NQO1 were performed. The results were shown in FIG. 3.

Example 3 [Expression and Purification of Fusion Protein DE24-HRV3Csite-NQO1 (Construct 3; pI=4.78)]

Peptide tag 3 (DE24) was fused to the N-terminal side of NQO1 that is a target protein, and expression and purification of a fusion protein containing HRV3Csite between NQO1 and DE24 were performed.

(1) Construction of pM01_DE24 Vector

A pM01_DE24 vector in which a polynucleotide encoding peptide tag DE24 was inserted into a pM01 vector was constructed as below.

The polynucleotide (SEQ ID NO.: 34) encoding peptide tag 6 (DED; SEQ ID NO.: 6) and primers 4F (SEQ ID NO.: 35) and 4R (SEQ ID NO.: 36) corresponding to the insert part were prepared, and the insert part was amplified using KOD-Plus-(TOYOBO CO., LTD.) as a PCR enzyme, under the same PCR conditions as in Example 1. The amplified PCR product was migrated by 1.0% (w/v) agarose electrophoresis, and the part matched to the length of the insert part was cut out from the gel and purified to prepare an insert part. A SmaI site of the pM01 vector (SYSMEX CORPORATION) was treated with SmaI (TAKARA BIO INC.), and the insert part was inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37°

C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pM01_DE24.

(2) pM01_DE24 HRV3Csite_NQO1 was constructed, and a recombinant baculovirus was prepared in the same manner as in Example 1, then expression, purification and detection of fusion protein DE24-HRV3Csite-NQO1 were performed. The results were shown in FIG. 4.

Example 4 [Expression and Purification of Fusion Protein DE30-HRV3Csite-NQO1 (Construct 4; pI=4.61)]

Peptide tag 4 (DE30) was fused to the N-terminal side of NQO1 that is a target protein, and expression and purification of a fusion protein containing HRV3Csite between NQO1 and DE30 were performed.

The same procedures were carried out as in Example 1, except for preparing an insert part using polynucleotides (SEQ ID NOs.: 37 and 38) encoding DE30 (SEQ ID NO.: 4) in place of the polynucleotides encoding the peptide tag DE12, to construct a pM01_DE30 vector.

Further, pM01_DE30 HRV3Csite_NQO1 was constructed, and a recombinant baculovirus was prepared in the same manner as in Example 1, then expression, purification and detection of fusion protein DE30-HRV3Csite-NQO1 were performed. The results were shown in FIG. 5.

Example 5 [Expression and Purification of Fusion Protein DE36-HRV3Csite-NQO1 (Construct 5; pI=4.49)]

Peptide tag 5 (DE36) was fused to the N-terminal side of NQO1 that is a target protein, and expression and purification of a fusion protein containing HRV3Csite between NQO1 and DE36 were performed.

The same procedures were carried out as in Example 1, except for preparing an insert part using polynucleotides (SEQ ID NOs.: 39 and 40) encoding DE36 (SEQ ID NO.: 5) in place of the polynucleotides encoding the peptide tag DE12, to construct a pM01_DE36 vector.

Further, pM01_DE36_HRV3Csite_NQO1 was constructed, and a recombinant baculovirus was prepared in the same manner as in Example 1, then expression, purification and detection of fusion protein DE36-HRV3Csite-NQO1 were performed. The results were shown in FIG. 6.

Example 6 [Expression and Purification of Fusion Protein DED-HRV3Csite-NQO1 (Construct 6; pI=4.26)]

Peptide tag 6 (DED) was fused to the N-terminal side of NQO1 that is a target protein, and expression and purification of a fusion protein containing HRV3Csite between NQO1 and DED were performed.

(1) Construction of pHS01_DED Vector

A pHS01_DED vector in a peptide tag DED (SEQ ID NO.: 6) was inserted into a pHS01 vector was constructed as below.

The polynucleotide (SEQ ID NO.: 34) encoding the peptide tag DED and primers 5F (SEQ ID NO.: 41) and 5R (SEQ ID NO.: 42) corresponding to the insert part were prepared, and the insert part was amplified using KOD-Plus- (TOYOBO CO., LTD.) as a PCR enzyme, under the same PCR conditions as in Example 1. The amplified PCR product was migrated by 1.0% (w/v) agarose electrophoresis, and the part matched to the length of the insert part was cut out from the gel and purified to prepare an insert part. A NheI site of the pHS01 vector (SYSMEX CORPORATION) was treated with NheI (TAKARA BIO INC.), and the insert part was inserted using In-Fusion HD Cloning Kit (Clontech Laboratories, Inc.). Stellar Competent Cells were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pHS01_DED.

(2) HS01_DED_HRV3Csite_NQO1 was constructed, and a recombinant baculovirus was prepared in the same manner as in Example 1, then expression, purification and detection of fusion protein DED-HRV3Csite-NQO1 were performed. The results were shown in FIG. 7.

Example 7 [Expression and Purification of Fusion Protein DES-HRV3Csite-NQO1 (Construct 7; pI=4.55)]

Peptide tag 7 (DES) was fused to the N-terminal side of NQO1 that is a target protein, and expression and purification of a fusion protein containing HRV3Csite between NQO1 and DES were performed.

The same procedures were carried out as in Example 6, except for using primers 6F (SEQ ID NO.: 43) and 6R (SEQ ID NO.: 44) as the primers corresponding to the insert part, to construct pHS01_DES.

pHS01_DES_HRV3Csite_NQO1 was constructed, and a recombinant baculovirus was prepared in the same manner as in Example 1, then expression, purification and detection of fusion protein DES-HRV3Csite-NQO1 were performed. The results were shown in FIG. 8.

Example 8 [Expression and Purification of Fusion Protein EO24-HRV3Csite-NQO1 (Construct 8; pI=4.73)]

Peptide tag 8 (EO24) was fused to the N-terminal side of NQO1 that is a target protein, and expression and purification of a fusion protein containing HRV3Csite between NQO1 and EO24 were performed.

(1) Construction of pHS01_EO24

Polynucleotides encoding peptide tag EO24 (SEQ ID NOs.: 45 and 46) were annealed in pairs to prepare an insert part. A NheI site of the pHS01 vector (SYSMEX CORPORATION) was treated with NheI (TAKARA BIO INC.), and the insert part was inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pHS01_EO24.

(2) pHS01_EO24_HRV3Csite_NQO1 was constructed, and a recombinant baculovirus was prepared in the same manner as in Example 1, then expression, purification and detection of fusion protein EO24-HRV3Csite-NQO1 were performed. The results were shown in FIG. 9.

Example 9 [Expression and Purification of Fusion Protein NQO1-HRV3Csite-DED (Construct 9; pI=4.26)]

The peptide tag DED was fused to the C-terminal side of NQO1 that is a target protein, and expression and purification of a fusion protein containing HRV3Csite between NQO1 and DED were performed.

(1) Construction of pHS02_DED Vector pHS02_DE12 Vector in which a polynucleotide encoding the peptide tag DED was inserted into pHS02 vector was constructed as below.

The polynucleotide (SEQ ID NO.: 34) encoding the peptide tag DED and primers 7F (SEQ ID NO.: 47) and 7R (SEQ ID NO.: 48) corresponding to the insert part were prepared, and the insert part was amplified using KOD-Plus-(TOYOBO CO., LTD.) as a PCR enzyme, under the same PCR conditions as in Example 1. The amplified PCR product was migrated by 1.0% (w/v) agarose electrophoresis, and the part matched to the length of the insert part was cut out from the gel and purified to prepare an insert part. A NheI site of the pHS02 vector (SYSMEX CORPORATION) was treated with NheI (TAKARA BIO INC.), and the insert part was inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pHS02_DED.

(2) The same procedures were carried out as in Example 1, except for using primers 8F (SEQ ID NO.: 49) and 8R (SEQ ID NO.: 50) as the primers corresponding to the insert part, to construct pHS02_NQO1 HRV3Csite_DED.

(3) Further, a recombinant baculovirus was prepared in the same manner as in Example 1, and expression, purification and detection of fusion protein NQO1-HRV3Csite-DED were performed. The results were shown in FIG. 10.

Example 10 [Expression and Purification of Fusion Protein NQO1-HRV3Csite-DES (Construct 10; pI=4.55)]

Peptide tag DES was fused to the C-terminal side of NQO1 that is a target protein, and expression and purification of a fusion protein containing HRV3Csite between NQO1 and DES were performed.

(1) The same procedures were carried out as in Example 9, except for using 9F (SEQ ID NO.: 51) and 9R (SEQ ID NO.: 52) as the primers, to construct pHS02_DES.

(2) The same procedures were carried out as in Example 9 to construct pHS01_NQO1_HRV3Csite_DES.

(3) A recombinant baculovirus was prepared in the same manner as in Example 1, and expression, purification and detection of fusion protein NQO1-HRV3Csite-DES were performed. The results were shown in FIG. 11.

Example 11 [Expression and Purification of Fusion Protein DED-HRV3Csite-Luciferase (Construct 11; pI=4.47)]

(1) Construction of pHS01_DED Vector

The same procedures were carried out as in Example 6 to construct pHS01_DED.

(2) Construction of pHS01_DED_HRV3Csite_Luciferase

The polynucleotide (SEQ ID NO.: 53) encoding Luciferase and primers 10F (SEQ ID NO.: 54) and 10R (SEQ ID NO.: 55) corresponding to the insert part were prepared, and the insert part was amplified using KOD-Plus-(TOYOBO CO., LTD.) as a PCR enzyme, under the same PCR conditions as in Example 1. The amplified PCR product was migrated by 1.0% (w/v) agarose electrophoresis, and the part matched to the length of the insert part was cut out from the gel and purified to prepare an insert part. A SmaI site of the pHS01_DED vector was treated with SmaI (TAKARA BIO INC.), and the insert part was inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pHS01_DED_HRV3Csite_Luciferase.

(3) A recombinant baculovirus was prepared in the same manner as in Example 1, and expression, purification and detection of fusion protein DED-HRV3Csite-Luciferase were performed. The results were shown in FIG. 12.

Example 12 [Expression and Purification of Fusion Protein DES-HRV3Csite-Luciferase (Construct 12; pI=4.75)]

The same procedures were carried out as in Example 11, except for using a pHS01_DES vector constructed in Example 7 in place of the pHS01_DED vector, to construct pHS02_DES_HRV3Csite_Luciferase.

A recombinant baculovirus was prepared in the same manner as in Example 1, and expression, purification and detection of fusion protein DES-HRV3Csite-Luciferase were performed. The results were shown in FIG. 13.

Example 13 [Expression and Purification of Fusion Protein DED-HRV3C (Construct 13; pI=4.75)]

(1) Construction of pET17b_DED_HRV3C

The polynucleotide (SEQ ID NO.: 34) encoding the peptide tag DED, a polynucleotide (SEQ ID NO.: 56) encoding HRV3C, primers 11F and 11R (SEQ ID NOs.: 57 and 58; DED) corresponding to the insert part and primers 12F and 12R (SEQ ID NOs.: 59 and 60; HRV3C) were prepared, and the insert part was amplified using KOD-Plus- (TOYOBO CO., LTD.) as a PCR enzyme, under the same PCR conditions as in Example 1. The amplified PCR product was migrated by 1.0% (w/v) agarose electrophoresis, and the part matched to the length of the insert part was cut out from the gel and purified to prepare an insert part. A SmaI site and a NheI site of the pHS01 vector (SYSMEX CORPORATION) were treated with SmaI (TAKARA BIO INC.) and NheI (TAKARA BIO INC.), and the two insert parts were inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 1 and 2 for sequence confirmation, then the base sequence was analyzed by a DNA sequencer (Thermo Fisher Scientific Inc.). A vector into which the insert part was introduced, that had no variation in other part, was defined as pHS01_DED_HRV3C.

Next, an insert for pET17b was prepared. Primers 13F (SEQ ID NO.: 61) and 13R (SEQ ID NO.: 62) were prepared, and the primers were amplified using pHS01_DED_HRV3C as a template, and using KOD-Plus- (TOYOBO CO., LTD.) as a PCR enzyme, under the same PCR conditions as in Example 1. The amplified PCR product was migrated by 1.0% (w/v) agarose electrophoresis, and the part matched to the length of the insert part was cut out from the gel and purified to prepare an insert part. A NdeI site of the pET17b Vector (Novagen, Inc.) was treated with NdeI (TAKARA BIO INC.), and the insert part was inserted using In-Fusion HD Cloning Kit (Clontech Laboratories, Inc.). Stellar Competent Cells (Clontech Laboratories, Inc.) were transformed with the constructed vector, then the obtained transformant was seeded on a LBA plate. The transformant was cultured at 37° C. for 16 hrs. An ampicillin resistant transformant was selected from the obtained transformants according to normal procedure, and purification of plasmid was performed. In order to confirm a base sequence of the selected clone, the PCR reaction was performed by Big Dye Terminator v3.1 (Thermo Fisher Scientific Inc.), using primers 14 (SEQ ID NO.: 63) and 15 (SEQ ID NO.: 64) for sequence confirmation, then the base sequence was analyzed by a DNA sequencer (Thermo Fisher Scientific Inc.). A vector into which the insert part was introduced, that had no variation in other part, was defined as pET17b_DED_HRV3C.

(2) Expression and Purification of DED-HRV3C

E. coli was transformed using pET17b_DED_HRV3C, and 1.5 L of an LB medium containing ampicillin was cultured at 37° C. and cooled to 15° C. around a turbidity OD of about 0.6, then IPTG was added thereto to induce expression of protein. After 16 hours, bacteria were collected by centrifugation (8,000 g, 15 minutes) and frozen at −80° C. 120 mL of a buffer (20 mM Tris-HCl (pH 8.0), 150 mM NaCl, 1 tablet Complete EDTA free (Roche)) was added to the frozen E. coli, and E. coli was crushed by ultrasonic wave. The crushed solution was centrifuged (15,000 g×30 minutes), then the supernatant fraction was filtered with 0.8 uM of a filter agent, and the filtrate was collected. The filtrate was loaded on an ion exchange resin (Hitrap Q HP (1 mL)), and purified using a mixed solution of 20 mM Tris-HCl (pH 8.0, 150 mM NaCl; buffer A) and 20 mM Tris-HCl (pH 8.0, 1000 mM NaCl; buffer B). First, only buffer A (NaCl concentration of 150 mM) was flown through the ion exchange resin (EL0), and a fraction eluted with a 3:1 mixed solution of buffer A:buffer B (NaCl concentration of 363 mM) (EL1), a fraction eluted with a 1:1 mixed solution of buffer A:buffer B (NaCl concentration of 575 mM) (EL2), a fraction eluted with a 1:3 mixed solution of buffer A:buffer B (NaCl concentration of 788 mM) (EL3), and finally, a fraction eluted with only buffer B (NaCl concentration of 1000 mM) (EL4) were each collected.

Figure 14:
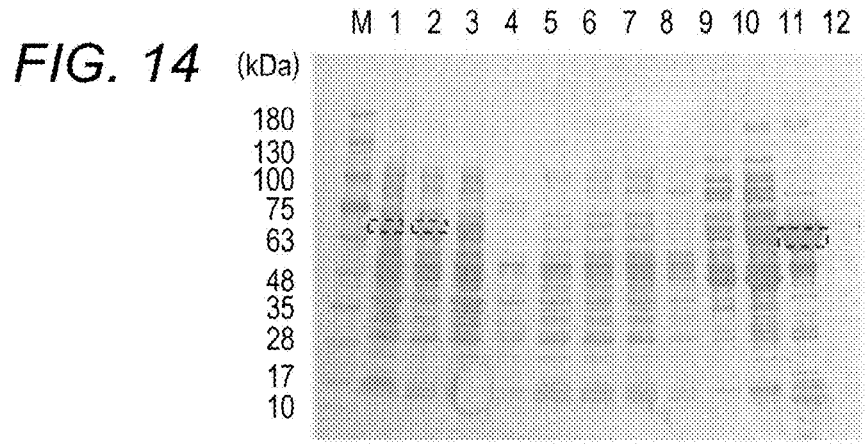
FIG. 14 is a figure showing the results of SDS-PAGE in Example 13.
Figure 15:
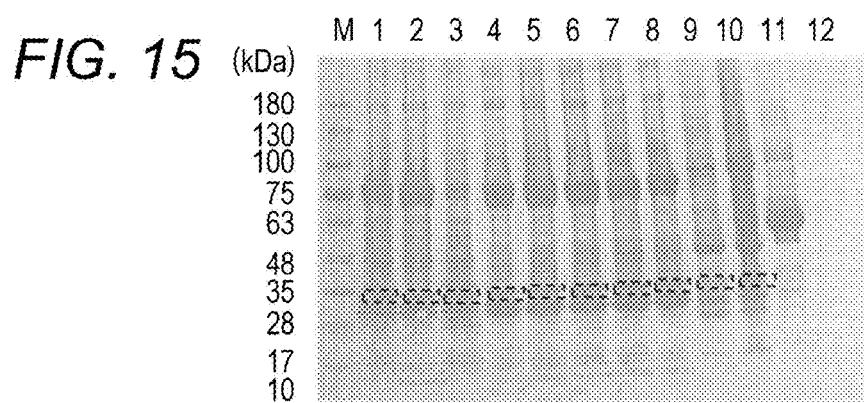
FIG. 15 is a figure showing the results of SDS-PAGE in Comparative Example 1.

(3) The same procedures were carried out as in Example 1 to detect a fusion protein. The results were shown in FIG. 14. In FIG. 14, the results of electrophoresis are shown as follows; M: molecular weight marker, lane 1: homogenate solution, lane 2: supernatant fraction after centrifugation, lane 3: precipitated fraction after centrifugation, lanes 4 to 7: flow-through fractions 1 to 4 of the ion exchange resin, lane 8: elution fraction by buffer A (NaCl concentration of 150 mM) (EL0), lane 9: elution fraction by a 3:1 mixed solution of buffer A:buffer B (NaCl concentration of 363 mM) (EL1), lane 10: elution fraction by a 1:1 mixed solution of buffer A:buffer B (NaCl concentration of 575 mM) (EL2), lane 11: elution fraction by a 1:3 mixed solution of buffer A:buffer B (NaCl concentration of 788 mM) (EL3), and lane 12: elution fraction by buffer B (NaCl concentration of 1000 mM) (EL4).

Comparative Example 1 [Expression and Purification of Fusion Protein DE6-HRV3Csite-NQO1 (pI=6.4)]

Peptide tag DE6 was fused to the N-terminal side of NQO1 that is a target protein, and expression and purification of a fusion protein containing HRV3Csite between NQO1 and DE6 were performed.

The same procedures were carried out as in Example 1, except for preparing an insert part using polynucleotides (SEQ ID NOs.: 66 and 67) encoding DE6 (EEEDDD; SEQ ID NO.: 65) in place of the polynucleotides encoding the peptide tag DE12, to construct a pM01_DE6 vector.

Further, pM01_DE6_HRV3Csite_NQO1 was constructed, and a recombinant baculovirus was prepared in the same manner as in Example 1, then expression, purification and detection of fusion protein DE6-HRV3Csite-NQO1 were performed. The results were shown in FIG. 15.

(Regarding Results of Examples 1 to 13 and Comparative Example 1)

In Comparative Example 1 (DE6-HRV3Csite-NQO1, pI=6.4), a fusion protein was contained in every fraction, and separation was insufficient. On the other hand, Examples 1 to 13 all showed good separation. Particularly, a fusion protein binding a peptide tag with 18 or more acidic amino acid residues was held in the ion exchange resin up to a high salt concentration of 500 mM or more, and separation from contaminant proteins was improved (Examples 2 to 13). Also in all three target proteins, good separation was obtained (Examples 6 to 7 and 11 to 13). The peptide tag, even the peptide tag containing both aspartic acid residue and glutamic acid residue as acidic amino acid residues, or the peptide tag containing only either one, equally showed good separation (Examples 3 and 8). Even when the binding position of the peptide tag is either N-terminal side or C-terminal side of the target protein, separation was good (Examples 6 to 7 and 9 to 10).

Example 14 [Separation and Detection of Target Protein NQ1 from Fusion Protein DE12-HRV3Csite-NQO1]

Protease DED-HRV3C was reacted with DE12-HRV3Csite-NQO1 to cleave DE12 from DE12-HRV3Csite-NQO1.

To Fraction EL2 collected in Example 1 was mixed a 1/10 volume of Fraction EL3 collected in Example 13, and the mixture was allowed to stand at 4° C. After 16 hours, 20 mM Tris-HCl (pH 8.0) was added to this reaction solution to be diluted to a NaCl concentration of about 250 mM, and the diluted solution was loaded on an ion exchange resin (Hitrap Q HP (1 mL)) equilibrated with 20 mM Tris-HCl (pH 8.0), 150 mM NaCl. Flow-through fractions were collected (Fr. 1 to 6 (NaCl concentration of about 250 mM)), and fractions finally eluted (Fr. 7 to 10) with only buffer B (NaCl concentration of about 1000 mM) were each collected.

Figure 16:
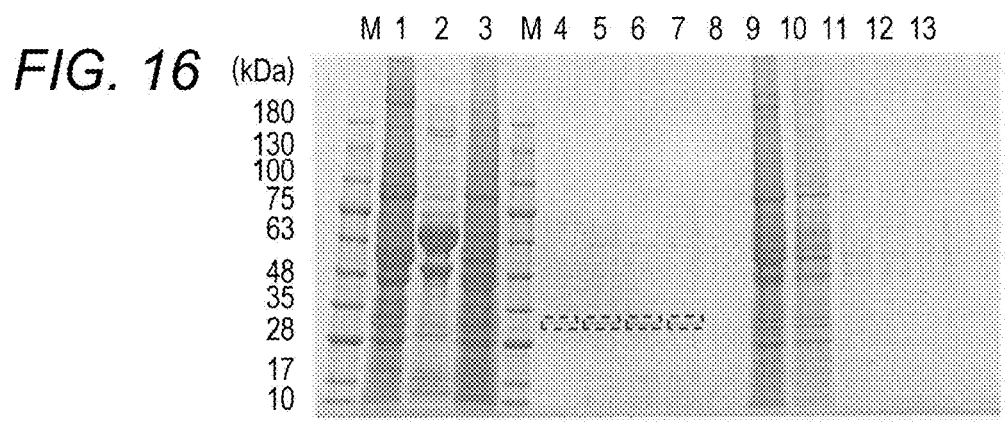
FIG. 16 is a figure showing the results of SDS-PAGE in Example 14.
Figure 17:
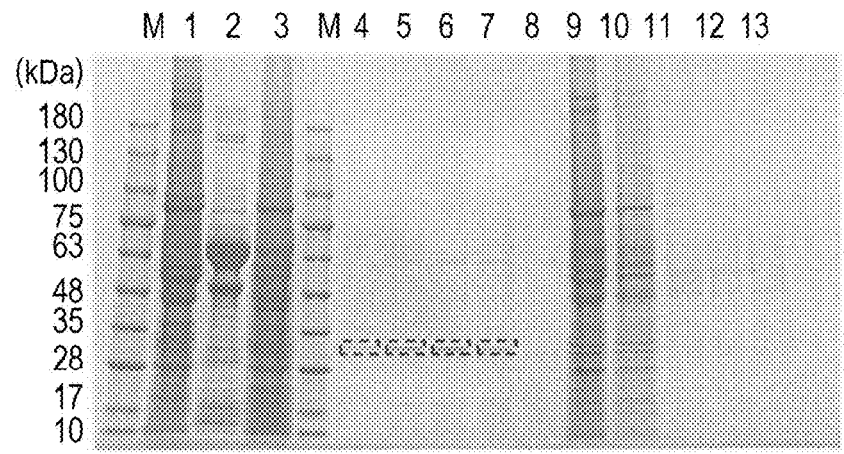
FIG. 17 is a figure showing the results of SDS-PAGE in Example 15.
Figure 18:
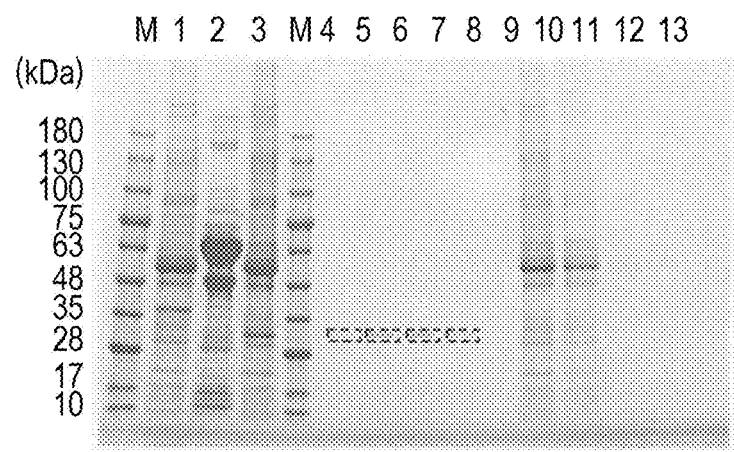
FIG. 18 is a figure showing the results of SDS-PAGE in Example 16.
Figure 19:
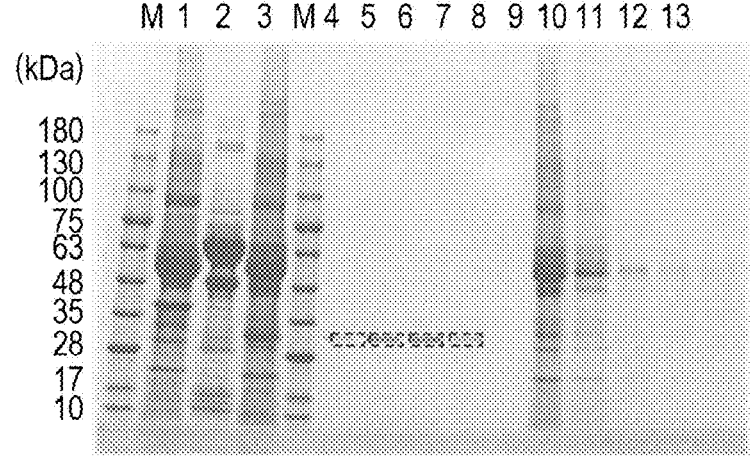
FIG. 19 is a figure showing the results of SDS-PAGE in Example 17.
Figure 20:
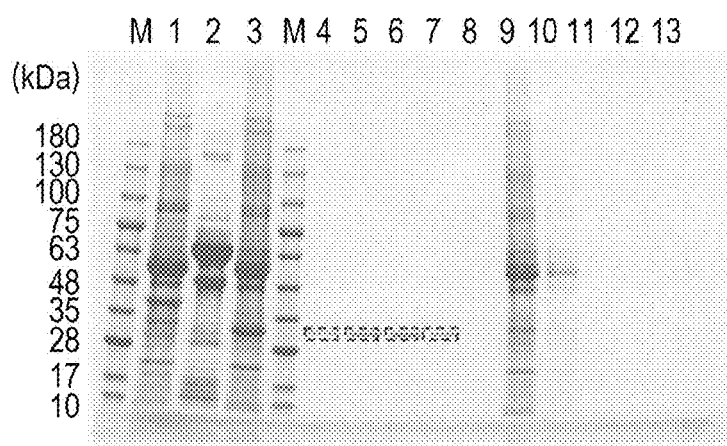
FIG. 20 is a figure showing the results of SDS-PAGE in Example 18.
Figure 21:
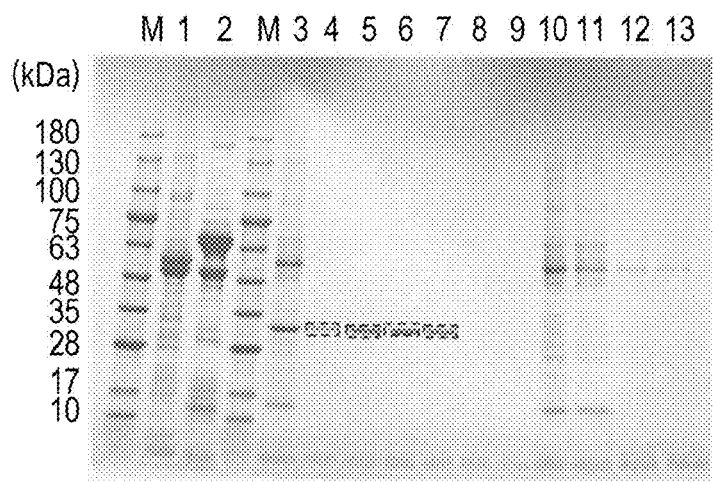
FIG. 21 is a figure showing the results of SDS-PAGE in Example 19.
Figure 22:
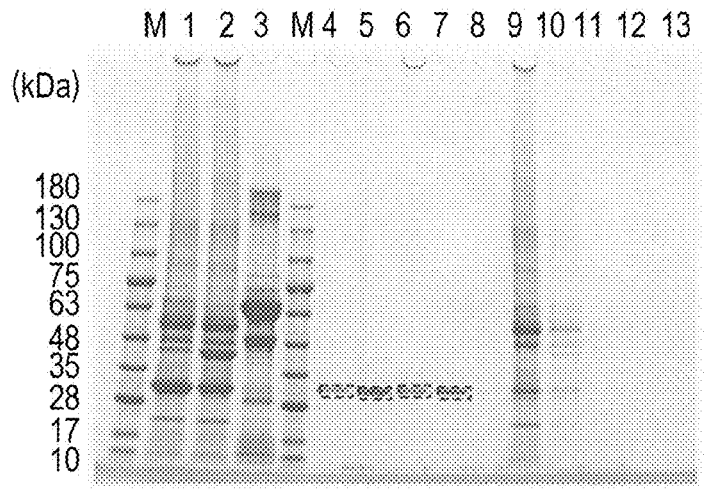
FIG. 22 is a figure showing the results of SDS-PAGE in Example 20.
Figure 23:
FIG. 23 is a figure showing the results of SDS-PAGE in Example 21.
Figure 24:
FIG. 24 is a figure showing the results of SDS-PAGE in Example 22.
Figure 25:
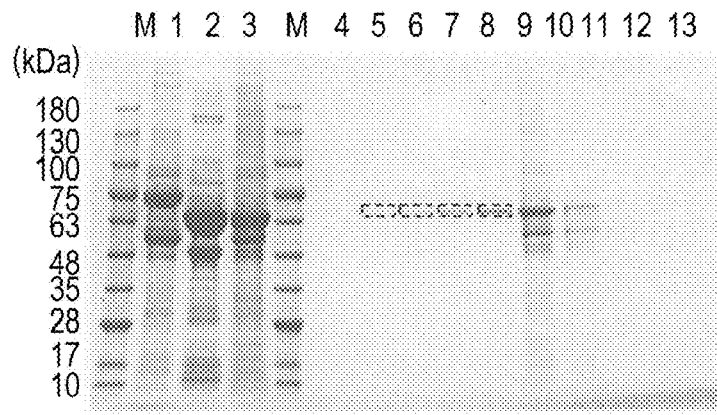
FIG. 25 is a figure showing the results of SDS-PAGE in Example 23.

SDS-PAGE was performed using 5 to 20% gradient gel and an electrophoresis apparatus (APRO Science Inc.). Each collected fraction and β-ME Sample Treatment for Tris SDS (COSMO BIO Co., Ltd.) were mixed in a volume ratio of 1:1, and treated at 100° C. for 3 minutes, then 5 uL of the resulting solution was loaded on the gel. As a molecular weight marker, 2.5 uL of Blue Star (NIPPON Genetics Co, Ltd.) was loaded on the gel. The gel loaded with the sample was migrated at a voltage of 400 V for 14 minutes, and then the gel was stained by GelCode Blue Stain Reagent (Thermo Fisher Scientific Inc.), and excess staining was bleached, then the image was photographed using Gel Doc XR+ system (Bio-Rad Laboratories, Inc.). The results were shown in FIG. 16. In FIG. 16, the results of electrophoresis are shown as follows; M: molecular weight marker, lane 1: EL2 (Examples 1 and 8) or EL3 (Examples 2 to 7 and 11 to 12), lane 2: EL3 of Example 13, lane 3: a mixed reaction liquid of EL2 or EL3 of Examples 1 to 12, and EL3 of Example 13, lanes 4 to 8: flow-through fractions 1 to 5 of the ion exchange resin, and lanes 9 to 13: elution fractions 1 to 5 by buffer B. Explanation of each lane is common in FIGS. 17 to 25.

Example 15

The same procedures were carried out as in Example 14, except for using EL2 of Example 2 in place of EL2 of Example 1, to detect a target protein NQO1. The results were shown in FIG. 17.

Example 16

The same procedures were carried out as in Example 14, except for using EL3 of Example 3 in place of EL2 of Example 1, to detect a target protein NQO1. The results were shown in FIG. 18.

Example 17

The same procedures were carried out as in Example 14, except for using EL3 of Example 4 in place of EL2 of Example 1, to detect a target protein NQO1. The results were shown in FIG. 19.

Example 18

The same procedures were carried out as in Example 14, except for using EL3 of Example 5 in place of EL2 of Example 1, to detect a target protein NQO1. The results were shown in FIG. 20.

Example 19

The same procedures were carried out as in Example 14, except for using EL3 of Example 6 in place of EL2 of Example 1, to detect a target protein NQO1. The results were shown in FIG. 21.

Example 20

The same procedures were carried out as in Example 14, except for using EL3 of Example 7 in place of EL2 of Example 1, to detect a target protein NQO1. The results were shown in FIG. 22.

Example 21

The same procedures were carried out as in Example 14, except for using EL2 of Example 8 in place of EL2 of Example 1, to detect a target protein NQO1. The results were shown in FIG. 23.

Example 22

The same procedures were carried out as in Example 14, except for using EL3 of Example 11 in place of EL2 of Example 1, to detect a target protein Luciferase. The results were shown in FIG. 24.

Example 23

The same procedures were carried out as in Example 14, except for using EL3 of Example 12 in place of EL2 of Example 1, to detect a target protein Luciferase. The results were shown in FIG. 25.

(Regarding Results of Examples 14 to 23)

Based on the results of Examples 14 to 23, it was shown that the protease is reacted with the fusion protein, whereby a target protein NQO1 or Luciferase can be acquired in the flow-through fraction of the anion exchange resin.

Example 24 [Evaluation of Effect on Separation Due to pH of Buffer]

The same procedures were carried out as in Example 6 to construct pHS01_DED_HRV3Csite_NQO1.

pHS01_DED_HRV3Csite_NQO1 and baculovirus DNA were introduced into silkworm culture cells (BmN cells), and homologous recombination of virus was performed. The culture cells were cultured for 6 days, and the recombinant virus was collected. Thereafter, a virus solution diluted 50 times with MilliQ water was inoculated into pupa of silkworm, and the pupa was incubated for 6 days. The pupa of silkworm was collected, and 50 mL of a buffer (20 mM PIPES (pH 6.1), 150 mM NaCl, 1 tablet Complete EDTA free (Roche), phenylthiourea) was added per a pupa to homogenate the pupa. The solution was centrifuged (8,000 g, 10 minutes), then the supernatant fraction was filtered with 0.8 uM of a filter agent, and the filtrate was collected. The filtrate was loaded on an ion exchange resin (Hitrap Q HP (1 mL)), and purified using a mixed solution of 20 mM PIPES (pH 6.1, 150 mM NaCl; buffer C) and 20 mM PIPES (pH 6.1, 1000 mM NaCl; buffer D). First, only buffer C (NaCl concentration of 150 mM) was flown through the ion exchange resin (EL0), and a fraction eluted with a solution with a mixing ratio of buffer C:buffer D of 3:1 (NaCl concentration of 363 mM) (EL1), a fraction eluted with a solution with a mixing ratio of 1:1 of buffer C:buffer D (NaCl concentration of 575 mM) (EL2), a fraction eluted with a solution with a mixing ratio of 1:3 of buffer C:buffer D (NaCl concentration of 788 mM) (EL3), and finally, a fraction eluted with only buffer D (NaCl concentration of 1000 mM) (EL4) were each collected.

Figure 26:
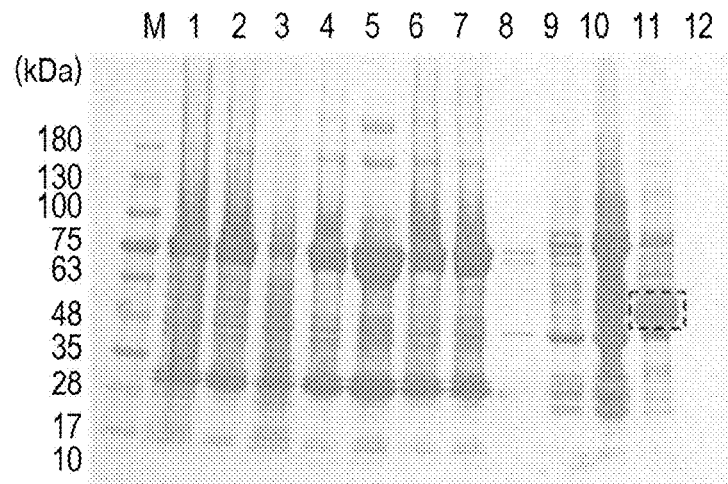
FIG. 26 is a figure showing the results of SDS-PAGE in Example 24.
Figure 27:
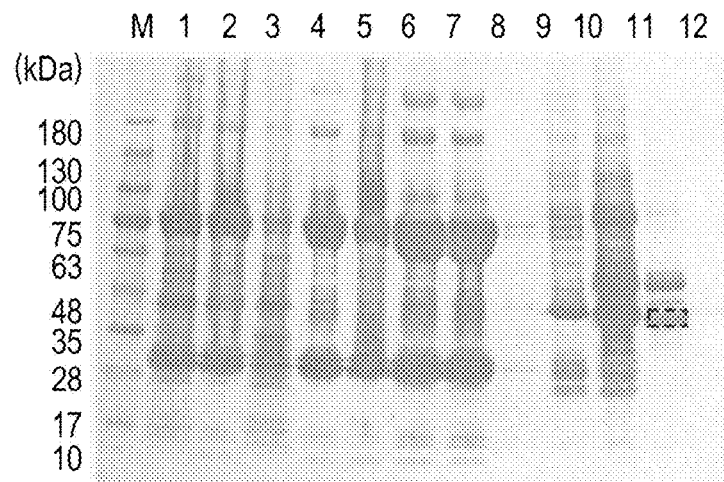
FIG. 27 is a figure showing the results of SDS-PAGE in Example 25.
Figure 28:
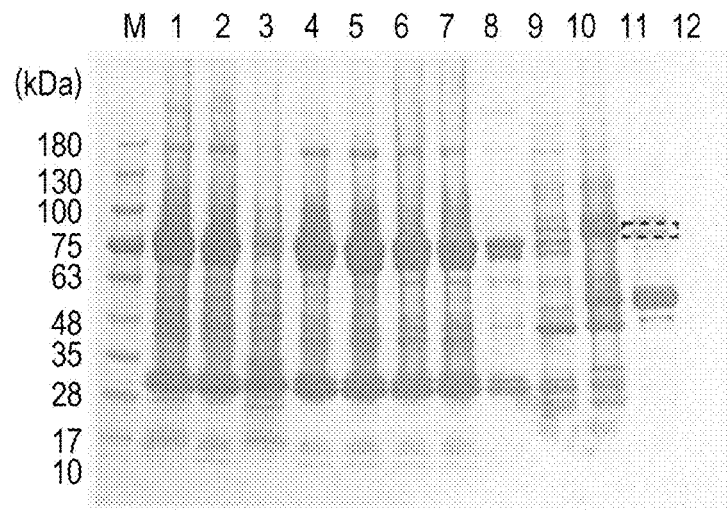
FIG. 28 is a figure showing the results of SDS-PAGE in Example 26.

The same procedures were carried out as in Example 1 to detect DED-HRV3Csite-NQO1. The results were shown in FIG. 26. In FIG. 26, the results of electrophoresis are shown as follows; M: molecular weight marker, lane 1: homogenate solution, lane 2: supernatant fraction after centrifugation, lane 3: precipitated fraction after centrifugation, lanes 4 to 7: flow-through fractions 1 to 4 of the ion exchange resin, lane 8: elution fraction by buffer C (NaCl concentration of 150 mM) (EL0), lane 9: elution fraction by a 3:1 mixed solution of buffer C:buffer D (NaCl concentration of 363 mM) (EL1), lane 10: elution fraction by a 1:1 mixed solution of buffer C:buffer D (NaCl concentration of 575 mM) (EL2), lane 11: elution fraction by a 1:3 mixed solution of buffer C:buffer D (NaCl concentration of 788 mM) (EL3), and lane 12: elution fraction by buffer D (NaCl concentration of 1000 mM) (EL4). Explanation of each lane is common in FIGS. 27 to 28.

Example 25

The same procedures were carried out as in Example 7 to construct pHS01_DES_HRV3Csite_NQO1.

Furthermore, the same procedures were carried out as in Example 24 to express, purify and detect DES-HRV3Csite-NQO1. The results were shown in FIG. 27.

Example 26

The same procedures were carried out as in Example 11 to construct pHS01_DED_HRV3Csite_Luciferase.

Furthermore, the same procedures were carried out as in Example 24 to express, purify and detect DED-HRV3Csite-Luciferase. The results were shown in FIG. 28.

Example 27

The same procedures were carried out as in Example 7 to construct pHS01_DES_HRV3Csite_NQO1.

*E. coli* was transformed using pHS01_DES_HRV3Csite_NQO1, and 1.5 L of an LB medium containing ampicillin was cultured at 37° C. and cooled to 15° C. around a turbidity OD of about 0.6, then IPTG was added thereto to induce expression of protein. After 16 hours, bacteria were collected by centrifugation (8,000 g, 15 minutes) and frozen at −80° C. 120 mL of a buffer (20 mM PIPES (pH 6.1), 150 mM NaCl, 1 tablet Complete EDTA free (Roche)) was added to the frozen *E. coli*, and *E. coli* was crushed by ultrasonic wave. The crushed solution was centrifuged (15,000 g×30 minutes), then the supernatant fraction was filtered with 0.8 uM of a filter agent, and the filtrate was collected. The filtrate was loaded on an ion exchange resin (Hitrap Q HP (1 mL)), and purified using a mixed solution of 20 mM PIPES (pH 6.1, 150 mM NaCl; buffer C) and 20 mM PIPES (pH 6.1, 1000 mM NaCl; buffer D). First, only buffer C (NaCl concentration of 150 mM) was flown through the ion exchange resin (EL0), and a fraction eluted with a 3:1 mixed solution of buffer C:buffer D (NaCl concentration of 363 mM) (EL1), a fraction eluted with a 1:1 mixed solution of buffer C:buffer D (NaCl concentration of 575 mM) (EL2), a fraction eluted with a 1:3 mixed solution of buffer C:buffer D (NaCl concentration of 788 mM) (EL3), and finally, a fraction eluted with only buffer D (NaCl concentration of 1000 mM) (EL4) were each collected.

Figure 29:
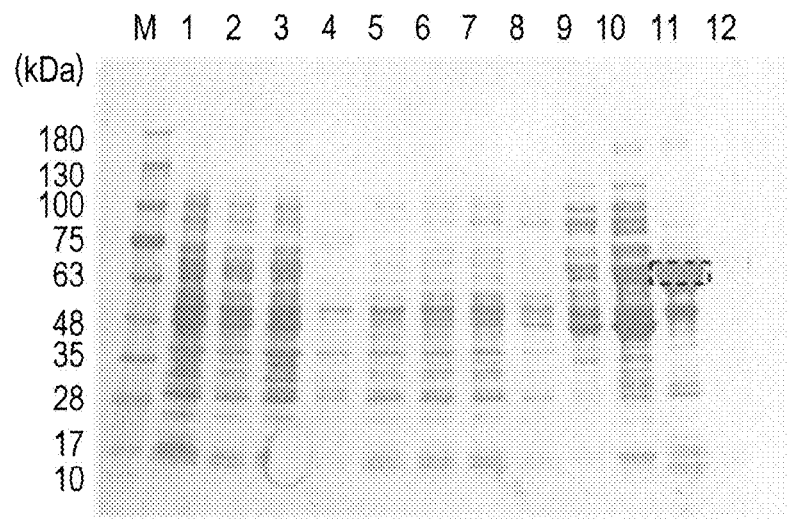
FIG. 29 is a figure showing the results of SDS-PAGE in Example 27.

The same procedures were carried out as in Example 1 to detect DED-HRV3Csite-NQO1. The results were shown in FIG. 29. In FIG. 29, the results of electrophoresis are shown as follows; M: molecular weight marker, lane 1: homogenate solution, lane 2: supernatant fraction after centrifugation, lane 3: precipitated fraction after centrifugation, lanes 4 to 7: flow-through fractions 1 to 4 of the ion exchange resin, lane 8: elution fraction by buffer C (NaCl concentration of 150 mM) (EL0), lane 9: elution fraction by a 3:1 mixed solution of buffer C:buffer D (NaCl concentration of 363 mM) (EL1), lane 10: elution fraction by a 1:1 mixed solution of buffer C:buffer D (NaCl concentration of 575 mM) (EL2), lane 11: elution fraction by a 1:3 mixed solution of buffer C:buffer D (NaCl concentration of 788 mM) (EL3), and lane 12: elution fraction by buffer D (NaCl concentration of 1000 mM; EL4).

Example 28

To EL3 of Example 24 was added a 1/10 volume of EL3 of Example 27, and the mixture was allowed to stand at 4° C. After 16 hours, 20 mM PIPES (pH 6.1) was added to the reaction solution to be diluted to a NaCl concentration of about 250 mM, and the diluted solution was loaded on an ion exchange resin (Hitrap Q HP (1 mL)) equilibrated with 20 mM PIPES (pH 6.1, 150 mM NaCl). Flow-through fractions were collected (Fr. 1 to 6 (NaCl concentration of about 250 mM)), and fractions finally eluted (Fr. 7 to 10) with only buffer D (NaCl concentration of about 1000 mM) were each collected.

Figure 30:
FIG. 30 is a figure showing the results of SDS-PAGE in Example 28.

The same procedures were carried out as in Example 1 to detect a target protein EQO1. The results were shown in FIG. 30. In FIG. 30, the results of electrophoresis are shown as follows; M: molecular weight marker, lane 1: EL3 of Example 24, lane 2: EL3 of Example 27, lane 3: a mixed reaction liquid of EL3 of Example 24, and EL3 of Example 27, lanes 4 to 8: flow-through fractions 1 to 5 of the ion exchange resin, and lanes 9 to 13: elution fractions 1 to 5 by buffer D.

(Regarding Results of Examples 24 to 28)

Based on the results of Examples 24 to 28, it was shown that, in the expression and purification of the fusion protein and purification of the target protein, good separation is obtained even the pH of the buffer is lowered.

What is claimed is:

1. A method for purifying a target protein, comprising steps of bringing a fusion protein comprising an amino acid sequence of a polyanionic peptide tag, an amino acid sequence of a cleavable site of a protease and an amino acid sequence of a target protein, into contact with a tagged protease comprising an amino acid sequence of a polyanionic peptide tag and an amino acid sequence of the protease in a solution, to cleave the polyanionic peptide tag from the fusion protein, and bringing the solution comprising the polyanionic peptide tag cleaved from the fusion protein, the target protein and the tagged protease into contact with an anion exchange resin to separate the target protein from the polyanionic peptide tag cleaved from the fusion protein and the tagged protease, thereby obtaining a solution comprising the target protein, wherein in the fusion protein, the amino acid sequence of the cleavable site is located between the amino acid sequence of the polyanionic peptide tag and the amino acid sequence of the target protein, and the polyanionic peptide tag of the tagged protease includes the amino acid sequence NVEGKTGNAT (residues 4-13 of SEQ ID NO: 7) and the amino acid sequence SGA (residues 41-43 of SEQ ID NO: 7).

2. The method for purifying a target protein according to claim 1, wherein the polyanionic peptide tag of the tagged protease comprises 2 or more acidic amino acid residues which are located between the amino acid sequence NVEGKTGNAT (residues 4-13 of SEQ ID NO: 7) and the amino acid sequence SGA (residues 41-43 of SEQ ID NO: 7).

3. The method for purifying a target protein according to claim 1, wherein the polyanionic peptide tag of the fusion protein and the polyanionic peptide tag of the protease comprise the amino acid sequence of SEQ ID NO: 6 or 7.

4. The method for purifying a target protein according to claim 1, wherein the polyanionic peptide tag is separated from the fusion protein, thereby generating a difference between the isoelectric point of the fusion protein and the isoelectric point of the target protein, and based on the difference in the isoelectric point, the target protein and the polyanionic peptide tag are separated.

5. The method for purifying a target protein according to claim 1, wherein the isoelectric point of the fusion protein is less than 6, and the isoelectric point of the protease is less than 6.

6. The method for purifying a target protein according to claim 1, wherein the salt concentration of the solution comprising the polyanionic peptide tag, the target protein and the tagged protease is 100 mM or more and 500 mM or less.

7. The method for purifying a target protein according to claim 1, wherein a step of removing contaminant proteins is conducted before the step of separating the polyanionic peptide tag from the fusion protein.

8. The method for purifying a target protein according to claim 7, further comprising, before the step of removing contaminant proteins, steps of introducing a vector comprising a polynucleotide encoding the fusion protein into a host cell, and expressing the fusion protein in the host cell to prepare a sample solution comprising the fusion protein and the contaminant proteins.

9. The method for purifying a target protein according to claim 7, wherein, in the step of removing contaminant proteins, the sample solution comprising the fusion protein and the contaminant proteins is brought into contact with an ion exchange resin to separate the fusion protein and the contaminant proteins, thereby removing the contaminant proteins.

10. The method for purifying a target protein according to claim 7, wherein the salt concentration of the sample solution is 50 mM or more and 500 mM or less.

11. The method for purifying a target protein according to claim 7, wherein the removing step comprises steps of obtaining (i) an anion exchange resin to which the fusion protein is bound and (ii) a flow-through fraction comprising the contaminant proteins, by passing the sample solution through the anion exchange resin, and removing the flow-through fraction.

12. The method according to claim 11, wherein the removing step comprises, after the obtaining (i) and (ii), a step of eluting the fusion protein from the anion exchange resin using a buffer with a salt concentration of 600 mM or more, by passing the buffer through the anion exchange resin.

13. The method for purifying a target protein according to claim 7, wherein the polyanionic peptide tag comprises 12 or more acidic amino acid residues.

14. A method for purifying a target protein, comprising steps of preparing a sample comprising a fusion protein and contaminant proteins, wherein the fusion protein comprises an amino acid sequence of a polyanionic peptide tag, an amino acid sequence of a cleavable site of a protease and an amino acid sequence of a target protein, wherein the amino acid sequence of the cleavable site is located between the amino acid sequence of the polyanionic peptide tag and the amino acid sequence of the target protein,
  passing the sample through an anion exchange resin to obtain (i) the anion exchange resin to which the fusion protein is bound and (ii) a flow-through fraction comprising the contaminant proteins,
  removing the flow-through fraction,
  passing a buffer through the anion exchange resin to elute the fusion protein from the anion exchange resin to obtain a flow-through fraction comprising the fusion protein,
  bringing the fusion protein in the flow-through fraction into contact with a tagged protease comprising an amino acid sequence of a polyanionic peptide tag and an amino acid sequence of the protease in a solution, to cleave the polyanionic peptide tag from the fusion protein,
  bringing the solution comprising the polyanionic peptide tag cleaved from the fusion protein, the target protein and the tagged protease into contact with an anion exchange resin to separate the target protein from the polyanionic peptide tag cleaved from the fusion protein and the tagged protease, whereby the polyanionic peptide tag cleaved from the fusion protein and the tagged protease are bound to the anion exchange resin and a flow-through fraction comprising the target protein is obtained,
  wherein the polyanionic peptide tag of the tagged protease includes the amino acid sequence NVEGKTGNAT (residues 4-13 of SEQ ID NO: 7) and the amino acid sequence SGA (residues 41-43 of SEQ ID NO: 7).

* * * * *

SEQUENCE LISTING

<160> NUMBER OF SEQ ID NOS: 67

<210> SEQ ID NO 1
<211> LENGTH: 12

```
<212> TYPE: PRT
<213> ORGANISM: Artificial Sequence
<220> FEATURE:
<223> OTHER INFORMATION: Synthetic sequence DE12

<400> SEQUENCE: 1

Glu Glu Glu Glu Glu Glu Asp Asp Asp Asp Asp Asp
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic sequence DE18

<400> SEQUENCE: 2

Glu Glu Glu Glu Glu Glu Glu Glu Glu Asp Asp Asp Asp Asp Asp
1               5                   10                  15

Asp Asp Asp

<210> SEQ ID NO 3
<211> LENGTH: 24
<212> TYPE: PRT
<213> ORGANISM: Artificial Sequence
<220> FEATURE:
<223> OTHER INFORMATION: Synthetic sequence DE24

<400> SEQUENCE: 3

Glu Glu Glu Glu Glu Glu Glu Glu Glu Glu Glu Glu Asp Asp Asp Asp
1               5                   10                  15

Asp Asp Asp Asp Asp Asp Asp Asp
            20

<210> SEQ ID NO 4
<211> LENGTH: 30
<212> TYPE: PRT
<213> ORGANISM: Artificial Sequence
<220> FEATURE:
<223> OTHER INFORMATION: Synthetic sequence DE30

<400> SEQUENCE: 4

Glu Glu Glu Glu Glu Glu Glu Glu Glu Glu Glu Glu Glu Glu Glu Asp
1               5                   10                  15

Asp Asp Asp Asp Asp Asp Asp Asp Asp Asp Asp Asp Asp Asp
            20                  25                  30

<210> SEQ ID NO 5
<211> LENGTH: 36
<212> TYPE: PRT
<213> ORGANISM: Artificial Sequence
<220> FEATURE:
<223> OTHER INFORMATION: Synthetic sequence DE36

<400> SEQUENCE: 5

Glu Glu Glu Glu Glu Glu Glu Glu Glu Glu Glu Glu Glu Glu Glu Glu
1               5                   10                  15

Glu Glu Asp Asp Asp Asp Asp Asp Asp Asp Asp Asp Asp Asp
            20                  25                  30

Asp Asp Asp Asp
            35

<210> SEQ ID NO 6
<211> LENGTH: 88
```

```
<212> TYPE: PRT
<213> ORGANISM: Artificial Sequence
<220> FEATURE:
<223> OTHER INFORMATION: Synthetic sequence DED

<400> SEQUENCE: 6

Asn Val Glu Gly Lys Thr Gly Asn Ala Thr Asp Glu Glu Glu Glu
1               5                   10                  15

Glu Glu Glu Glu Glu Glu Glu Asp Asp Asp Asp Asp Asp Asp Asp
                20                  25                  30

Asp Asp Asp Glu Asp Ser Gly Ala Glu Ile Gln Asp Asp Glu Glu
            35                  40                  45

Gly Phe Asp Asp Glu Glu Glu Phe Asp Asp Asp Asp Asp Glu His
        50                  55                  60

Asp Asp Asp Asp Leu Glu Asn Glu Glu Asn Glu Leu Glu Glu Leu Glu
65                  70                  75                  80

Glu Arg Val Glu Ala Arg Lys Lys
                85

<210> SEQ ID NO 7
<211> LENGTH: 44
<212> TYPE: PRT
<213> ORGANISM: Artificial Sequence
<220> FEATURE:
<223> OTHER INFORMATION: Synthetic sequence DES

<400> SEQUENCE: 7

Asp Leu Ser Asn Val Glu Gly Lys Thr Gly Asn Ala Thr Asp Glu Glu
1               5                   10                  15

Glu Glu Glu Glu Glu Glu Glu Glu Glu Asp Asp Asp Asp Asp
                20                  25                  30

Asp Asp Asp Asp Asp Asp Glu Asp Ser Gly Ala Glu
            35                  40

<210> SEQ ID NO 8
<211> LENGTH: 24
<212> TYPE: PRT
<213> ORGANISM: Artificial Sequence
<220> FEATURE:
<223> OTHER INFORMATION: Synthetic sequence E024

<400> SEQUENCE: 8

Glu Glu Glu Glu Glu Glu Glu Glu Glu Glu Glu Glu Glu Glu Glu
1               5                   10                  15

Glu Glu Glu Glu Glu Glu Glu Glu Glu
                20

<210> SEQ ID NO 9
<211> LENGTH: 274
<212> TYPE: PRT
<213> ORGANISM: Artificial Sequence
<220> FEATURE:
<223> OTHER INFORMATION: Synthetic sequence NQ01

<400> SEQUENCE: 9

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Ala Leu Lys Lys
                20                  25                  30

Lys Gly Trp Glu Val Val Glu Ser Asp Leu Tyr Ala Met Asn Phe Asn
            35                  40                  45
```

```
Pro Ile Ile Ser Arg Lys Asp Ile Thr Gly Lys Leu Lys Asp Pro Ala
 50                  55                  60

Asn Phe Gln Tyr Pro Ala Glu Ser Val Leu Ala Tyr Lys Glu Gly His
 65                  70                  75                  80

Leu Ser Pro Asp Ile Val Ala Glu Gln Lys Lys Leu Glu Ala Ala Asp
                 85                  90                  95

Leu Val Ile Phe Gln Phe Pro Leu Gln Trp Phe Gly Val Pro Ala Ile
                100                 105                 110

Leu Lys Gly Trp Phe Glu Arg Val Phe Ile Gly Glu Phe Ala Tyr Thr
            115                 120                 125

Tyr Ala Ala Met Tyr Asp Lys Gly Pro Phe Arg Ser Lys Lys Ala Val
130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
        195                 200                 205

Lys Lys Arg Leu Glu Asn Ile Trp Asp Glu Thr Pro Leu Tyr Phe Ala
210                 215                 220

Pro Ser Ser Leu Phe Asp Leu Asn Phe Gln Ala Gly Phe Leu Met Lys
225                 230                 235                 240

Lys Glu Val Gln Asp Glu Glu Lys Asn Lys Lys Phe Gly Leu Ser Val
                245                 250                 255

Gly His His Leu Gly Lys Ser Ile Pro Thr Asp Asn Gln Ile Lys Ala
            260                 265                 270

Arg Lys

<210> SEQ ID NO 10
<211> LENGTH: 546
<212> TYPE: PRT
<213> ORGANISM: Artificial Sequence
<220> FEATURE:
<223> OTHER INFORMATION: Synthetic luciferase sequence

<400> SEQUENCE: 10

Glu Asp Ala Lys Asn Ile Lys Lys Gly Pro Ala Pro Phe Tyr Pro Leu
 1               5                  10                  15

Glu Asp Gly Thr Ala Gly Glu Gln Leu His Lys Ala Met Lys Arg Tyr
                 20                  25                  30

Ala Leu Val Pro Gly Thr Ile Ala Phe Thr Asp Ala His Ile Glu Val
            35                  40                  45

Asn Ile Thr Tyr Ala Glu Tyr Phe Glu Met Ser Val Arg Leu Ala Glu
 50                  55                  60

Ala Met Lys Arg Tyr Gly Leu Asn Thr Asn His Arg Ile Val Val Cys
 65                  70                  75                  80

Ser Glu Asn Ser Leu Gln Phe Phe Met Pro Val Leu Gly Ala Leu Phe
                 85                  90                  95

Ile Gly Val Ala Val Ala Pro Ala Asn Asp Ile Tyr Asn Glu Arg Glu
            100                 105                 110

Leu Leu Asn Ser Met Asn Ile Ser Gln Pro Thr Val Val Phe Val Ser
        115                 120                 125

Lys Lys Gly Leu Gln Lys Ile Leu Asn Val Gln Lys Lys Leu Pro Ile
```

```
            130                 135                 140
Ile Gln Lys Ile Ile Ile Met Asp Ser Lys Thr Asp Tyr Gln Gly Phe
145                 150                 155                 160

Gln Ser Met Tyr Thr Phe Val Thr Ser His Leu Pro Pro Gly Phe Asn
                165                 170                 175

Glu Tyr Asp Phe Val Pro Glu Ser Phe Asp Arg Asp Lys Thr Ile Ala
            180                 185                 190

Leu Ile Met Asn Ser Ser Gly Ser Thr Gly Leu Pro Lys Gly Val Ala
            195                 200                 205

Leu Pro His Arg Thr Ala Cys Val Arg Phe Ser His Ala Arg Asp Pro
        210                 215                 220

Ile Phe Gly Asn Gln Ile Ile Pro Asp Thr Ala Ile Leu Ser Val Val
225                 230                 235                 240

Pro Phe His His Gly Phe Gly Met Phe Thr Thr Leu Gly Tyr Leu Ile
                245                 250                 255

Cys Gly Phe Arg Val Val Leu Met Tyr Arg Phe Glu Glu Glu Leu Phe
            260                 265                 270

Leu Arg Ser Leu Gln Asp Tyr Lys Ile Gln Ser Ala Leu Leu Val Pro
        275                 280                 285

Thr Leu Phe Ser Phe Phe Ala Lys Ser Thr Leu Ile Asp Lys Tyr Asp
    290                 295                 300

Leu Ser Asn Leu His Glu Ile Ala Ser Gly Gly Ala Pro Leu Ser Lys
305                 310                 315                 320

Glu Val Gly Glu Ala Val Ala Lys Arg Phe His Leu Pro Gly Ile Arg
                325                 330                 335

Gln Gly Tyr Gly Leu Thr Glu Thr Thr Ser Ala Ile Leu Ile Thr Pro
            340                 345                 350

Glu Gly Asp Asp Lys Pro Gly Ala Val Gly Lys Val Val Pro Phe Phe
        355                 360                 365

Glu Ala Lys Val Val Asp Leu Asp Thr Gly Lys Thr Leu Gly Val Asn
    370                 375                 380

Gln Arg Gly Glu Leu Cys Val Arg Gly Pro Met Ile Met Ser Gly Tyr
385                 390                 395                 400

Val Asn Asn Pro Glu Ala Thr Asn Ala Leu Ile Asp Lys Asp Gly Trp
                405                 410                 415

Leu His Ser Gly Asp Ile Ala Tyr Trp Asp Glu Asp Glu His Phe Phe
            420                 425                 430

Ile Val Asp Arg Leu Lys Ser Leu Ile Lys Tyr Lys Gly Tyr Gln Val
        435                 440                 445

Ala Pro Ala Glu Leu Glu Ser Ile Leu Leu Gln His Pro Asn Ile Phe
    450                 455                 460

Asp Ala Gly Val Ala Gly Leu Pro Asp Asp Ala Gly Glu Leu Pro
465                 470                 475                 480

Ala Ala Val Val Val Leu Glu His Gly Lys Thr Met Thr Glu Lys Glu
                485                 490                 495

Ile Val Asp Tyr Val Ala Ser Gln Val Thr Thr Ala Lys Lys Leu Arg
            500                 505                 510

Gly Gly Val Val Phe Val Asp Glu Val Pro Lys Gly Leu Thr Gly Lys
        515                 520                 525

Leu Asp Ala Arg Lys Ile Arg Glu Ile Leu Ile Lys Ala Lys Lys Gly
    530                 535                 540

Gly Lys
545
```

<210> SEQ ID NO 11
<211> LENGTH: 202
<212> TYPE: PRT
<213> ORGANISM: Artificial Sequence
<220> FEATURE:
<223> OTHER INFORMATION: Synthetic sequence HRV3C

<400> SEQUENCE: 11

```
Asp Leu Val Pro Arg Gly Ser Pro Glu Phe Pro Gly Arg Leu Glu Arg
1               5                   10                  15

Pro His Arg Asp Gly Pro Asn Thr Glu Phe Ala Leu Ser Leu Leu Arg
            20                  25                  30

Lys Asn Ile Met Thr Ile Thr Thr Ser Lys Gly Glu Phe Thr Gly Leu
        35                  40                  45

Gly Ile His Asp Arg Val Cys Val Ile Pro Thr His Ala Gln Pro Gly
    50                  55                  60

Asp Asp Val Leu Val Asn Gly Gln Lys Ile Arg Val Lys Asp Lys Tyr
65                  70                  75                  80

Lys Leu Val Asp Pro Glu Asn Ile Asn Leu Glu Leu Thr Val Leu Thr
                85                  90                  95

Leu Asp Arg Asn Glu Lys Phe Arg Asp Ile Arg Gly Phe Ile Ser Glu
            100                 105                 110

Asp Leu Glu Gly Val Asp Ala Thr Leu Val Val His Ser Asn Asn Phe
        115                 120                 125

Thr Asn Thr Ile Leu Glu Val Gly Pro Val Thr Met Ala Gly Leu Ile
    130                 135                 140

Asn Leu Ser Ser Thr Pro Thr Asn Arg Met Ile Arg Tyr Asp Tyr Ala
145                 150                 155                 160

Thr Lys Thr Gly Gln Cys Gly Gly Val Leu Cys Ala Thr Gly Lys Ile
                165                 170                 175

Phe Gly Ile His Val Gly Gly Asn Gly Arg Gln Gly Phe Ser Ala Gln
            180                 185                 190

Leu Lys Lys Gln Tyr Phe Val Glu Lys Gln
        195                 200
```

<210> SEQ ID NO 12
<211> LENGTH: 298
<212> TYPE: PRT
<213> ORGANISM: Artificial Sequence
<220> FEATURE:
<223> OTHER INFORMATION: Synthetic sequence DE12-HRV3Csite-NQO1

<400> SEQUENCE: 12

```
Met Glu Glu Glu Glu Glu Glu Asp Asp Asp Asp Asp Lys Gly Thr
1               5                   10                  15

Leu Glu Val Leu Phe Gln Gly Pro Met Val Gly Arg Arg Ala Leu Ile
            20                  25                  30

Val Leu Ala His Ser Glu Arg Thr Ser Phe Asn Tyr Ala Met Lys Glu
        35                  40                  45

Ala Ala Ala Ala Ala Leu Lys Lys Lys Gly Trp Glu Val Val Glu Ser
    50                  55                  60

Asp Leu Tyr Ala Met Asn Phe Asn Pro Ile Ile Ser Arg Lys Asp Ile
65                  70                  75                  80

Thr Gly Lys Leu Lys Asp Pro Ala Asn Phe Gln Tyr Pro Ala Glu Ser
                85                  90                  95

Val Leu Ala Tyr Lys Glu Gly His Leu Ser Pro Asp Ile Val Ala Glu
```

```
            100                 105                 110
Gln Lys Lys Leu Glu Ala Ala Asp Leu Val Ile Phe Gln Phe Pro Leu
        115                 120                 125

Gln Trp Phe Gly Val Pro Ala Ile Leu Lys Gly Trp Phe Glu Arg Val
130                 135                 140

Phe Ile Gly Glu Phe Ala Tyr Thr Tyr Ala Ala Met Tyr Asp Lys Gly
145                 150                 155                 160

Pro Phe Arg Ser Lys Lys Ala Val Leu Ser Ile Thr Thr Gly Gly Ser
                165                 170                 175

Gly Ser Met Tyr Ser Leu Gln Gly Ile His Gly Asp Met Asn Val Ile
                180                 185                 190

Leu Trp Pro Ile Gln Ser Gly Ile Leu His Phe Cys Gly Phe Gln Val
            195                 200                 205

Leu Glu Pro Gln Leu Thr Tyr Ser Ile Gly His Thr Pro Ala Asp Ala
        210                 215                 220

Arg Ile Gln Ile Leu Glu Gly Trp Lys Lys Arg Leu Glu Asn Ile Trp
225                 230                 235                 240

Asp Glu Thr Pro Leu Tyr Phe Ala Pro Ser Ser Leu Phe Asp Leu Asn
                245                 250                 255

Phe Gln Ala Gly Phe Leu Met Lys Lys Glu Val Gln Asp Glu Lys
                260                 265                 270

Asn Lys Lys Phe Gly Leu Ser Val Gly His His Leu Gly Lys Ser Ile
            275                 280                 285

Pro Thr Asp Asn Gln Ile Lys Ala Arg Lys
        290                 295
```

<210> SEQ ID NO 13
<211> LENGTH: 304
<212> TYPE: PRT
<213> ORGANISM: Artificial Sequence
<220> FEATURE:
<223> OTHER INFORMATION: Synthetic sequence DE18-HRV3Csite-NQO1

<400> SEQUENCE: 13

```
Met Glu Glu Glu Glu Glu Glu Glu Asp Asp Asp Asp Asp
1               5                   10                  15

Asp Asp Asp Lys Gly Thr Leu Glu Val Leu Phe Gln Gly Pro Met Val
                20                  25                  30

Gly Arg Arg Ala Leu Ile Val Leu Ala His Ser Glu Arg Thr Ser Phe
            35                  40                  45

Asn Tyr Ala Met Lys Glu Ala Ala Ala Ala Leu Lys Lys Lys Gly
50                  55                  60

Trp Glu Val Val Glu Ser Asp Leu Tyr Ala Met Asn Phe Asn Pro Ile
65                  70                  75                  80

Ile Ser Arg Lys Asp Ile Thr Gly Lys Leu Lys Asp Pro Ala Asn Phe
                85                  90                  95

Gln Tyr Pro Ala Glu Ser Val Leu Ala Tyr Lys Glu Gly His Leu Ser
            100                 105                 110

Pro Asp Ile Val Ala Glu Gln Lys Lys Leu Glu Ala Ala Asp Leu Val
        115                 120                 125

Ile Phe Gln Phe Pro Leu Gln Trp Phe Gly Val Pro Ala Ile Leu Lys
    130                 135                 140

Gly Trp Phe Glu Arg Val Phe Ile Gly Glu Phe Ala Tyr Thr Tyr Ala
145                 150                 155                 160

Ala Met Tyr Asp Lys Gly Pro Phe Arg Ser Lys Lys Ala Val Leu Ser
```

```
                    165                 170                 175
Ile Thr Thr Gly Gly Ser Gly Ser Met Tyr Ser Leu Gln Gly Ile His
                180                 185                 190

Gly Asp Met Asn Val Ile Leu Trp Pro Ile Gln Ser Gly Ile Leu His
            195                 200                 205

Phe Cys Gly Phe Gln Val Leu Glu Pro Gln Leu Thr Tyr Ser Ile Gly
        210                 215                 220

His Thr Pro Ala Asp Ala Arg Ile Gln Ile Leu Glu Gly Trp Lys Lys
225                 230                 235                 240

Arg Leu Glu Asn Ile Trp Asp Glu Thr Pro Leu Tyr Phe Ala Pro Ser
                245                 250                 255

Ser Leu Phe Asp Leu Asn Phe Gln Ala Gly Phe Leu Met Lys Lys Glu
            260                 265                 270

Val Gln Asp Glu Glu Lys Asn Lys Lys Phe Gly Leu Ser Val Gly His
        275                 280                 285

His Leu Gly Lys Ser Ile Pro Thr Asp Asn Gln Ile Lys Ala Arg Lys
290                 295                 300
```

<210> SEQ ID NO 14
<211> LENGTH: 310
<212> TYPE: PRT
<213> ORGANISM: Artificial Sequence
<220> FEATURE:
<223> OTHER INFORMATION: Synthetic sequence DE24-HRV3Csite-NQO1

<400> SEQUENCE: 14

```
Met Glu Glu Glu Glu Glu Glu Glu Glu Glu Glu Asp Asp Asp
1               5                   10                  15

Asp Asp Asp Asp Asp Asp Asp Asp Lys Gly Thr Leu Glu Val Leu
            20                  25                  30

Phe Gln Gly Pro Met Val Gly Arg Arg Ala Leu Ile Val Leu Ala His
        35                  40                  45

Ser Glu Arg Thr Ser Phe Asn Tyr Ala Met Lys Glu Ala Ala Ala
    50                  55                  60

Ala Leu Lys Lys Lys Gly Trp Glu Val Val Glu Ser Asp Leu Tyr Ala
65                  70                  75                  80

Met Asn Phe Asn Pro Ile Ile Ser Arg Lys Asp Ile Thr Gly Lys Leu
                85                  90                  95

Lys Asp Pro Ala Asn Phe Gln Tyr Pro Ala Glu Ser Val Leu Ala Tyr
            100                 105                 110

Lys Glu Gly His Leu Ser Pro Asp Ile Val Ala Glu Gln Lys Lys Leu
        115                 120                 125

Glu Ala Ala Asp Leu Val Ile Phe Gln Phe Pro Leu Gln Trp Phe Gly
    130                 135                 140

Val Pro Ala Ile Leu Lys Gly Trp Phe Glu Arg Val Phe Ile Gly Glu
145                 150                 155                 160

Phe Ala Tyr Thr Tyr Ala Ala Met Tyr Asp Lys Gly Pro Phe Arg Ser
                165                 170                 175

Lys Lys Ala Val Leu Ser Ile Thr Thr Gly Gly Ser Gly Ser Met Tyr
            180                 185                 190

Ser Leu Gln Gly Ile His Gly Asp Met Asn Val Ile Leu Trp Pro Ile
        195                 200                 205

Gln Ser Gly Ile Leu His Phe Cys Gly Phe Gln Val Leu Glu Pro Gln
    210                 215                 220

Leu Thr Tyr Ser Ile Gly His Thr Pro Ala Asp Ala Arg Ile Gln Ile
```

-continued 225    230    235    240

Leu Glu Gly Trp Lys Lys Arg Leu Glu Asn Ile Trp Asp Glu Thr Pro
         245                 250                 255

Leu Tyr Phe Ala Pro Ser Ser Leu Phe Asp Leu Asn Phe Gln Ala Gly
         260                 265                 270

Phe Leu Met Lys Lys Glu Val Gln Asp Glu Lys Asn Lys Lys Phe
         275                 280                 285

Gly Leu Ser Val Gly His His Leu Gly Lys Ser Ile Pro Thr Asp Asn
         290                 295                 300

Gln Ile Lys Ala Arg Lys
305              310

<210> SEQ ID NO 15
<211> LENGTH: 316
<212> TYPE: PRT
<213> ORGANISM: Artificial Sequence
<220> FEATURE:
<223> OTHER INFORMATION: Synthetic sequence DE30-HRV3Csite-NQO1

<400> SEQUENCE: 15

Met Glu Glu Glu Glu Glu Glu Glu Glu Glu Glu Glu Glu
1               5                   10                  15

Asp Asp Asp Asp Asp Asp Asp Asp Asp Asp Asp Asp Asp Lys
         20                  25                  30

Gly Thr Leu Glu Val Leu Phe Gln Gly Pro Met Val Gly Arg Arg Ala
         35                  40                  45

Leu Ile Val Leu Ala His Ser Glu Arg Thr Ser Phe Asn Tyr Ala Met
50                  55                  60

Lys Glu Ala Ala Ala Ala Leu Lys Lys Lys Gly Trp Glu Val Val
65                  70                  75                  80

Glu Ser Asp Leu Tyr Ala Met Asn Phe Asn Pro Ile Ile Ser Arg Lys
                 85                  90                  95

Asp Ile Thr Gly Lys Leu Lys Asp Pro Ala Asn Phe Gln Tyr Pro Ala
             100                 105                 110

Glu Ser Val Leu Ala Tyr Lys Glu Gly His Leu Ser Pro Asp Ile Val
         115                 120                 125

Ala Glu Gln Lys Lys Leu Glu Ala Ala Asp Leu Val Ile Phe Gln Phe
     130                 135                 140

Pro Leu Gln Trp Phe Gly Val Pro Ala Ile Leu Lys Gly Trp Phe Glu
145                 150                 155                 160

Arg Val Phe Ile Gly Glu Phe Ala Tyr Thr Tyr Ala Ala Met Tyr Asp
                 165                 170                 175

Lys Gly Pro Phe Arg Ser Lys Lys Ala Val Leu Ser Ile Thr Thr Gly
             180                 185                 190

Gly Ser Gly Ser Met Tyr Ser Leu Gln Gly Ile His Gly Asp Met Asn
         195                 200                 205

Val Ile Leu Trp Pro Ile Gln Ser Gly Ile Leu His Phe Cys Gly Phe
     210                 215                 220

Gln Val Leu Glu Pro Gln Leu Thr Tyr Ser Ile Gly His Thr Pro Ala
225                 230                 235                 240

Asp Ala Arg Ile Gln Ile Leu Glu Gly Trp Lys Lys Arg Leu Glu Asn
                 245                 250                 255

Ile Trp Asp Glu Thr Pro Leu Tyr Phe Ala Pro Ser Ser Leu Phe Asp
             260                 265                 270

Leu Asn Phe Gln Ala Gly Phe Leu Met Lys Lys Glu Val Gln Asp Glu

-continued

```
                275                 280                 285
Glu Lys Asn Lys Lys Phe Gly Leu Ser Val Gly His His Leu Gly Lys
            290                 295                 300
Ser Ile Pro Thr Asp Asn Gln Ile Lys Ala Arg Lys
305                 310                 315

<210> SEQ ID NO 16
<211> LENGTH: 322
<212> TYPE: PRT
<213> ORGANISM: Artificial Sequence
<220> FEATURE:
<223> OTHER INFORMATION: Synthetic sequence DE36-HRV3Csite-NQO1

<400> SEQUENCE: 16

Met Glu Glu Glu Glu Glu Glu Glu Glu Glu Glu Glu Glu Glu Glu Glu
1               5                   10                  15

Glu Glu Glu Asp Asp Asp Asp Asp Asp Asp Asp Asp Asp Asp Asp Asp
                20                  25                  30

Asp Asp Asp Asp Lys Gly Thr Leu Glu Val Leu Phe Gln Gly Pro
            35                  40                  45

Met Val Gly Arg Arg Ala Leu Ile Val Leu Ala His Ser Glu Arg Thr
50                  55                  60

Ser Phe Asn Tyr Ala Met Lys Glu Ala Ala Ala Ala Leu Lys Lys
65                  70                  75                  80

Lys Gly Trp Glu Val Val Glu Ser Asp Leu Tyr Ala Met Asn Phe Asn
                85                  90                  95

Pro Ile Ile Ser Arg Lys Asp Ile Thr Gly Lys Leu Lys Asp Pro Ala
            100                 105                 110

Asn Phe Gln Tyr Pro Ala Glu Ser Val Leu Ala Tyr Lys Glu Gly His
            115                 120                 125

Leu Ser Pro Asp Ile Val Ala Glu Gln Lys Lys Leu Glu Ala Ala Asp
            130                 135                 140

Leu Val Ile Phe Gln Phe Pro Leu Gln Trp Phe Gly Val Pro Ala Ile
145                 150                 155                 160

Leu Lys Gly Trp Phe Glu Arg Val Phe Ile Gly Glu Phe Ala Tyr Thr
                165                 170                 175

Tyr Ala Ala Met Tyr Asp Lys Gly Pro Phe Arg Ser Lys Lys Ala Val
            180                 185                 190

Leu Ser Ile Thr Thr Gly Gly Ser Gly Ser Met Tyr Ser Leu Gln Gly
            195                 200                 205

Ile His Gly Asp Met Asn Val Ile Leu Trp Pro Ile Gln Ser Gly Ile
210                 215                 220

Leu His Phe Cys Gly Phe Gln Val Leu Glu Pro Gln Leu Thr Tyr Ser
225                 230                 235                 240

Ile Gly His Thr Pro Ala Asp Ala Arg Ile Gln Ile Leu Glu Gly Trp
                245                 250                 255

Lys Lys Arg Leu Glu Asn Ile Trp Asp Glu Thr Pro Leu Tyr Phe Ala
            260                 265                 270

Pro Ser Ser Leu Phe Asp Leu Asn Phe Gln Ala Gly Phe Leu Met Lys
            275                 280                 285

Lys Glu Val Gln Asp Glu Lys Asn Lys Lys Phe Gly Leu Ser Val
            290                 295                 300

Gly His His Leu Gly Lys Ser Ile Pro Thr Asp Asn Gln Ile Lys Ala
305                 310                 315                 320

Arg Lys
```

<210> SEQ ID NO 17
<211> LENGTH: 388
<212> TYPE: PRT
<213> ORGANISM: Artificial Sequence
<220> FEATURE:
<223> OTHER INFORMATION: Synthetic sequence DED-HRV3Csite-NQO1

<400> SEQUENCE: 17

```
Met Asp Tyr Lys Asp Asp Asp Lys Gly Met Ala Ser Asp Leu Ser
1               5                   10                  15

Asn Val Glu Gly Lys Thr Gly Asn Ala Thr Asp Glu Glu Glu Glu
            20                  25                  30

Glu Glu Glu Glu Glu Glu Asp Asp Asp Asp Asp Asp Asp
            35                  40                  45

Asp Asp Asp Glu Asp Ser Gly Ala Glu Ile Gln Asp Asp Glu Glu
50                  55                  60

Gly Phe Asp Asp Glu Glu Glu Phe Asp Asp Asp Asp Glu His
65                  70                  75                  80

Asp Asp Asp Asp Leu Glu Asn Glu Glu Asn Glu Leu Glu Glu Leu Glu
                85                  90                  95

Glu Arg Val Glu Ala Arg Lys Lys Ala Ser Leu Glu Val Leu Phe Gln
            100                 105                 110

Gly Pro Met Val Gly Arg Arg Ala Leu Ile Val Leu Ala His Ser Glu
            115                 120                 125

Arg Thr Ser Phe Asn Tyr Ala Met Lys Glu Ala Ala Ala Ala Leu
            130                 135                 140

Lys Lys Lys Gly Trp Glu Val Val Glu Ser Asp Leu Tyr Ala Met Asn
145                 150                 155                 160

Phe Asn Pro Ile Ile Ser Arg Lys Asp Ile Thr Gly Lys Leu Lys Asp
                165                 170                 175

Pro Ala Asn Phe Gln Tyr Pro Ala Glu Ser Val Leu Ala Tyr Lys Glu
            180                 185                 190

Gly His Leu Ser Pro Asp Ile Val Ala Glu Gln Lys Lys Leu Glu Ala
            195                 200                 205

Ala Asp Leu Val Ile Phe Gln Phe Pro Leu Gln Trp Phe Gly Val Pro
210                 215                 220

Ala Ile Leu Lys Gly Trp Phe Glu Arg Val Phe Ile Gly Glu Phe Ala
225                 230                 235                 240

Tyr Thr Tyr Ala Ala Met Tyr Asp Lys Gly Pro Phe Arg Ser Lys Lys
                245                 250                 255

Ala Val Leu Ser Ile Thr Thr Gly Gly Ser Gly Ser Met Tyr Ser Leu
            260                 265                 270

Gln Gly Ile His Gly Asp Met Asn Val Ile Leu Trp Pro Ile Gln Ser
            275                 280                 285

Gly Ile Leu His Phe Cys Gly Phe Gln Val Leu Glu Pro Gln Leu Thr
            290                 295                 300

Tyr Ser Ile Gly His Thr Pro Ala Asp Ala Arg Ile Gln Ile Leu Glu
305                 310                 315                 320

Gly Trp Lys Lys Arg Leu Glu Asn Ile Trp Asp Glu Thr Pro Leu Tyr
                325                 330                 335

Phe Ala Pro Ser Ser Leu Phe Asp Leu Asn Phe Gln Ala Gly Phe Leu
            340                 345                 350

Met Lys Lys Glu Val Gln Asp Glu Glu Lys Asn Lys Lys Phe Gly Leu
            355                 360                 365
```

-continued

Ser Val Gly His His Leu Gly Lys Ser Ile Pro Thr Asp Asn Gln Ile
    370                 375                 380

Lys Ala Arg Lys
385

<210> SEQ ID NO 18
<211> LENGTH: 341
<212> TYPE: PRT
<213> ORGANISM: Artificial Sequence
<220> FEATURE:
<223> OTHER INFORMATION: Synthetic sequence DES-HRV3Csite-NQO1

<400> SEQUENCE: 18

Met Asp Tyr Lys Asp Asp Asp Lys Gly Met Ala Ser Asp Leu Ser
1                5                  10                  15

Asn Val Glu Gly Lys Thr Gly Asn Ala Thr Asp Glu Glu Glu Glu
            20                  25                  30

Glu Glu Glu Glu Glu Glu Glu Asp Asp Asp Asp Asp Asp Asp
        35                  40                  45

Asp Asp Asp Glu Asp Ser Gly Ala Glu Ala Ser Leu Glu Val Leu Phe
50                  55                  60

Gln Gly Pro Met Val Gly Arg Arg Ala Leu Ile Val Leu Ala His Ser
65                  70                  75                  80

Glu Arg Thr Ser Phe Asn Tyr Ala Met Lys Glu Ala Ala Ala Ala
                85                  90                  95

Leu Lys Lys Lys Gly Trp Glu Val Val Glu Ser Asp Leu Tyr Ala Met
            100                 105                 110

Asn Phe Asn Pro Ile Ile Ser Arg Lys Asp Ile Thr Gly Lys Leu Lys
        115                 120                 125

Asp Pro Ala Asn Phe Gln Tyr Pro Ala Glu Ser Val Leu Ala Tyr Lys
    130                 135                 140

Glu Gly His Leu Ser Pro Asp Ile Val Ala Glu Gln Lys Lys Leu Glu
145                 150                 155                 160

Ala Ala Asp Leu Val Ile Phe Gln Phe Pro Leu Gln Trp Phe Gly Val
                165                 170                 175

Pro Ala Ile Leu Lys Gly Trp Phe Glu Arg Val Phe Ile Gly Glu Phe
            180                 185                 190

Ala Tyr Thr Tyr Ala Ala Met Tyr Asp Lys Gly Pro Phe Arg Ser Lys
        195                 200                 205

Lys Ala Val Leu Ser Ile Thr Thr Gly Gly Ser Gly Ser Met Tyr Ser
    210                 215                 220

Leu Gln Gly Ile His Gly Asp Met Asn Val Ile Leu Trp Pro Ile Gln
225                 230                 235                 240

Ser Gly Ile Leu His Phe Cys Gly Phe Gln Val Leu Glu Pro Gln Leu
                245                 250                 255

Thr Tyr Ser Ile Gly His Thr Pro Ala Asp Ala Arg Ile Gln Ile Leu
            260                 265                 270

Glu Gly Trp Lys Lys Arg Leu Glu Asn Ile Trp Asp Glu Thr Pro Leu
        275                 280                 285

Tyr Phe Ala Pro Ser Ser Leu Phe Asp Leu Asn Phe Gln Ala Gly Phe
    290                 295                 300

Leu Met Lys Lys Glu Val Gln Asp Glu Lys Asn Lys Lys Phe Gly
305                 310                 315                 320

Leu Ser Val Gly His His Leu Gly Lys Ser Ile Pro Thr Asp Asn Gln
                325                 330                 335

```
Ile Lys Ala Arg Lys
            340

<210> SEQ ID NO 19
<211> LENGTH: 321
<212> TYPE: PRT
<213> ORGANISM: Artificial Sequence
<220> FEATURE:
<223> OTHER INFORMATION: Synthetic sequence EO24-HRV3Csite-NQO1

<400> SEQUENCE: 19

Met Asp Tyr Lys Asp Asp Asp Lys Gly Met Ala Ser Glu Glu Glu
1               5                   10                  15

Glu Glu Glu Glu Glu Glu Glu Glu Glu Glu Glu Glu Glu Glu Glu
                20                  25                  30

Glu Glu Glu Glu Glu Ala Ser Leu Glu Val Leu Phe Gln Gly Pro Met
            35                  40                  45

Val Gly Arg Arg Ala Leu Ile Val Leu Ala His Ser Glu Arg Thr Ser
    50                  55                  60

Phe Asn Tyr Ala Met Lys Glu Ala Ala Ala Ala Leu Lys Lys Lys
65                  70                  75                  80

Gly Trp Glu Val Val Glu Ser Asp Leu Tyr Ala Met Asn Phe Asn Pro
                85                  90                  95

Ile Ile Ser Arg Lys Asp Ile Thr Gly Lys Leu Lys Asp Pro Ala Asn
            100                 105                 110

Phe Gln Tyr Pro Ala Glu Ser Val Leu Ala Tyr Lys Glu Gly His Leu
        115                 120                 125

Ser Pro Asp Ile Val Ala Glu Gln Lys Lys Leu Glu Ala Ala Asp Leu
130                 135                 140

Val Ile Phe Gln Phe Pro Leu Gln Trp Phe Gly Val Pro Ala Ile Leu
145                 150                 155                 160

Lys Gly Trp Phe Glu Arg Val Phe Ile Gly Glu Phe Ala Tyr Thr Tyr
                165                 170                 175

Ala Ala Met Tyr Asp Lys Gly Pro Phe Arg Ser Lys Lys Ala Val Leu
            180                 185                 190

Ser Ile Thr Thr Gly Gly Ser Gly Ser Met Tyr Ser Leu Gln Gly Ile
        195                 200                 205

His Gly Asp Met Asn Val Ile Leu Trp Pro Ile Gln Ser Gly Ile Leu
210                 215                 220

His Phe Cys Gly Phe Gln Val Leu Glu Pro Gln Leu Thr Tyr Ser Ile
225                 230                 235                 240

Gly His Thr Pro Ala Asp Ala Arg Ile Gln Ile Leu Glu Gly Trp Lys
                245                 250                 255

Lys Arg Leu Glu Asn Ile Trp Asp Glu Thr Pro Leu Tyr Phe Ala Pro
            260                 265                 270

Ser Ser Leu Phe Asp Leu Asn Phe Gln Ala Gly Phe Leu Met Lys Lys
        275                 280                 285

Glu Val Gln Asp Glu Glu Lys Asn Lys Lys Phe Gly Leu Ser Val Gly
290                 295                 300

His His Leu Gly Lys Ser Ile Pro Thr Asp Asn Gln Ile Lys Ala Arg
305                 310                 315                 320

Lys

<210> SEQ ID NO 20
<211> LENGTH: 386
```

```
<212> TYPE: PRT
<213> ORGANISM: Artificial Sequence
<220> FEATURE:
<223> OTHER INFORMATION: Synthetic sequence NQO1-HRV3Csite-DED

<400> SEQUENCE: 20
```

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Leu Lys Lys
            20                  25                  30

Lys Gly Trp Glu Val Val Glu Ser Asp Leu Tyr Ala Met Asn Phe Asn
            35                  40                  45

Pro Ile Ile Ser Arg Lys Asp Ile Thr Gly Lys Leu Lys Asp Pro Ala
50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Phe Pro Leu Gln Trp Phe Gly Val Pro Ala Ile
            100                 105                 110

Leu Lys Gly Trp Phe Glu Arg Val Phe Ile Gly Glu Phe Ala Tyr Thr
            115                 120                 125

Tyr Ala Ala Met Tyr Asp Lys Gly Pro Phe Arg Ser Lys Lys Ala Val
130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
            195                 200                 205

Lys Lys Arg Leu Glu Asn Ile Trp Asp Glu Thr Pro Leu Tyr Phe Ala
210                 215                 220

Pro Ser Ser Leu Phe Asp Leu Asn Phe Gln Ala Gly Phe Leu Met Lys
225                 230                 235                 240

Lys Glu Val Gln Asp Glu Glu Lys Asn Lys Lys Phe Gly Leu Ser Val
                245                 250                 255

Gly His His Leu Gly Lys Ser Ile Pro Thr Asp Asn Gln Ile Lys Ala
            260                 265                 270

Arg Lys Gly Leu Glu Val Leu Phe Gln Gly Pro Ala Ser Asp Leu Ser
            275                 280                 285

Asn Val Glu Gly Lys Thr Gly Asn Ala Thr Asp Glu Glu Glu Glu
290                 295                 300

Glu Glu Glu Glu Glu Glu Glu Asp Asp Asp Asp Asp Asp Asp Asp
305                 310                 315                 320

Asp Asp Asp Glu Asp Ser Gly Ala Glu Ile Gln Asp Asp Glu Glu
                325                 330                 335

Gly Phe Asp Asp Glu Glu Glu Phe Asp Asp Asp Asp Glu His
            340                 345                 350

Asp Asp Asp Asp Leu Glu Asn Glu Glu Asn Glu Leu Glu Glu Leu Glu
            355                 360                 365

Glu Arg Val Glu Ala Arg Lys Lys Ala Ser Asp Tyr Lys Asp Asp Asp
370                 375                 380

Asp Lys
385

<210> SEQ ID NO 21
<211> LENGTH: 339
<212> TYPE: PRT
<213> ORGANISM: Artificial Sequence
<220> FEATURE:
<223> OTHER INFORMATION: Synthetic sequence NQO1-HRV3Csite-DES

<400> SEQUENCE: 21

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Leu Lys Lys
            20                  25                  30

Lys Gly Trp Glu Val Val Glu Ser Asp Leu Tyr Ala Met Asn Phe Asn
            35                  40                  45

Pro Ile Ile Ser Arg Lys Asp Ile Thr Gly Lys Leu Lys Asp Pro Ala
50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Phe Pro Leu Gln Trp Phe Gly Val Pro Ala Ile
            100                 105                 110

Leu Lys Gly Trp Phe Glu Arg Val Phe Ile Gly Glu Phe Ala Tyr Thr
            115                 120                 125

Tyr Ala Ala Met Tyr Asp Lys Gly Pro Phe Arg Ser Lys Lys Ala Val
130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
            195                 200                 205

Lys Lys Arg Leu Glu Asn Ile Trp Asp Glu Thr Pro Leu Tyr Phe Ala
210                 215                 220

Pro Ser Ser Leu Phe Asp Leu Asn Phe Gln Ala Gly Phe Leu Met Lys
225                 230                 235                 240

Lys Glu Val Gln Asp Glu Glu Lys Asn Lys Lys Phe Gly Leu Ser Val
                245                 250                 255

Gly His His Leu Gly Lys Ser Ile Pro Thr Asp Asn Gln Ile Lys Ala
            260                 265                 270

Arg Lys Gly Leu Glu Val Leu Phe Gln Gly Pro Ala Ser Asp Leu Ser
            275                 280                 285

Asn Val Glu Gly Lys Thr Gly Asn Ala Thr Asp Glu Glu Glu Glu
290                 295                 300

Glu Glu Glu Glu Glu Glu Glu Asp Asp Asp Asp Asp Asp Asp Asp
305                 310                 315                 320

Asp Asp Asp Glu Asp Ser Gly Ala Glu Ala Ser Asp Tyr Lys Asp Asp
                325                 330                 335

Asp Asp Lys

<210> SEQ ID NO 22
<211> LENGTH: 660
<212> TYPE: PRT
<213> ORGANISM: Artificial Sequence
<220> FEATURE:
<223> OTHER INFORMATION: Synthetic sequence DED-HRV3Csite-Luciferase

<400> SEQUENCE: 22

```
Met Asp Tyr Lys Asp Asp Asp Lys Gly Met Ala Ser Asp Leu Ser
1               5                   10                  15

Asn Val Glu Gly Lys Thr Gly Asn Ala Thr Asp Glu Glu Glu Glu
                20                  25                  30

Glu Glu Glu Glu Glu Glu Glu Asp Asp Asp Asp Asp Asp Asp Asp
            35                  40                  45

Asp Asp Asp Glu Asp Ser Gly Ala Glu Ile Gln Asp Asp Glu Glu
        50                  55                  60

Gly Phe Asp Asp Glu Glu Glu Phe Asp Asp Asp Asp Asp Glu His
65                  70                  75                  80

Asp Asp Asp Asp Leu Glu Asn Glu Glu Asn Glu Leu Glu Glu Leu Glu
                85                  90                  95

Glu Arg Val Glu Ala Arg Lys Lys Ala Ser Leu Glu Val Leu Phe Gln
                100                 105                 110

Gly Pro Glu Asp Ala Lys Asn Ile Lys Lys Gly Pro Ala Pro Phe Tyr
            115                 120                 125

Pro Leu Glu Asp Gly Thr Ala Gly Glu Gln Leu His Lys Ala Met Lys
        130                 135                 140

Arg Tyr Ala Leu Val Pro Gly Thr Ile Ala Phe Thr Asp Ala His Ile
145                 150                 155                 160

Glu Val Asn Ile Thr Tyr Ala Glu Tyr Phe Glu Met Ser Val Arg Leu
                165                 170                 175

Ala Glu Ala Met Lys Arg Tyr Gly Leu Asn Thr Asn His Arg Ile Val
            180                 185                 190

Val Cys Ser Glu Asn Ser Leu Gln Phe Phe Met Pro Val Leu Gly Ala
        195                 200                 205

Leu Phe Ile Gly Val Ala Val Ala Pro Ala Asn Asp Ile Tyr Asn Glu
210                 215                 220

Arg Glu Leu Leu Asn Ser Met Asn Ile Ser Gln Pro Thr Val Val Phe
225                 230                 235                 240

Val Ser Lys Lys Gly Leu Gln Lys Ile Leu Asn Val Gln Lys Lys Leu
                245                 250                 255

Pro Ile Ile Gln Lys Ile Ile Ile Met Asp Ser Lys Thr Asp Tyr Gln
            260                 265                 270

Gly Phe Gln Ser Met Tyr Thr Phe Val Thr Ser His Leu Pro Pro Gly
        275                 280                 285

Phe Asn Glu Tyr Asp Phe Val Pro Glu Ser Phe Asp Arg Asp Lys Thr
290                 295                 300

Ile Ala Leu Ile Met Asn Ser Ser Gly Ser Thr Gly Leu Pro Lys Gly
305                 310                 315                 320

Val Ala Leu Pro His Arg Thr Ala Cys Val Arg Phe Ser His Ala Arg
                325                 330                 335

Asp Pro Ile Phe Gly Asn Gln Ile Ile Pro Asp Thr Ala Ile Leu Ser
            340                 345                 350

Val Val Pro Phe His His Gly Phe Gly Met Phe Thr Thr Leu Gly Tyr
        355                 360                 365

Leu Ile Cys Gly Phe Arg Val Val Leu Met Tyr Arg Phe Glu Glu Glu
```

```
    370                 375                 380

Leu Phe Leu Arg Ser Leu Gln Asp Tyr Lys Ile Gln Ser Ala Leu Leu
385                 390                 395                 400

Val Pro Thr Leu Phe Ser Phe Phe Ala Lys Ser Thr Leu Ile Asp Lys
                405                 410                 415

Tyr Asp Leu Ser Asn Leu His Glu Ile Ala Ser Gly Gly Ala Pro Leu
            420                 425                 430

Ser Lys Glu Val Gly Glu Ala Val Ala Lys Arg Phe His Leu Pro Gly
        435                 440                 445

Ile Arg Gln Gly Tyr Gly Leu Thr Glu Thr Thr Ser Ala Ile Leu Ile
    450                 455                 460

Thr Pro Glu Gly Asp Asp Lys Pro Gly Ala Val Gly Lys Val Val Pro
465                 470                 475                 480

Phe Phe Glu Ala Lys Val Val Asp Leu Asp Thr Gly Lys Thr Leu Gly
                485                 490                 495

Val Asn Gln Arg Gly Glu Leu Cys Val Arg Gly Pro Met Ile Met Ser
            500                 505                 510

Gly Tyr Val Asn Asn Pro Glu Ala Thr Asn Ala Leu Ile Asp Lys Asp
        515                 520                 525

Gly Trp Leu His Ser Gly Asp Ile Ala Tyr Trp Asp Glu Asp Glu His
    530                 535                 540

Phe Phe Ile Val Asp Arg Leu Lys Ser Leu Ile Lys Tyr Lys Gly Tyr
545                 550                 555                 560

Gln Val Ala Pro Ala Glu Leu Glu Ser Ile Leu Leu Gln His Pro Asn
                565                 570                 575

Ile Phe Asp Ala Gly Val Ala Gly Leu Pro Asp Asp Asp Ala Gly Glu
            580                 585                 590

Leu Pro Ala Ala Val Val Val Leu Glu His Gly Lys Thr Met Thr Glu
        595                 600                 605

Lys Glu Ile Val Asp Tyr Val Ala Ser Gln Val Thr Thr Ala Lys Lys
    610                 615                 620

Leu Arg Gly Gly Val Val Phe Val Asp Glu Val Pro Lys Gly Leu Thr
625                 630                 635                 640

Gly Lys Leu Asp Ala Arg Lys Ile Arg Glu Ile Leu Ile Lys Ala Lys
                645                 650                 655

Lys Gly Gly Lys
            660

<210> SEQ ID NO 23
<211> LENGTH: 613
<212> TYPE: PRT
<213> ORGANISM: Artificial Sequence
<220> FEATURE:
<223> OTHER INFORMATION: Synthetic sequence DES-HRV3Csite-Luciferase

<400> SEQUENCE: 23

Met Asp Tyr Lys Asp Asp Asp Asp Lys Gly Met Ala Ser Asp Leu Ser
1               5                   10                  15

Asn Val Glu Gly Lys Thr Gly Asn Ala Thr Asp Glu Glu Glu Glu Glu
            20                  25                  30

Glu Glu Glu Glu Glu Glu Glu Asp Asp Asp Asp Asp Asp Asp Asp Asp
        35                  40                  45

Asp Asp Asp Glu Asp Ser Gly Ala Glu Ala Ser Leu Glu Val Leu Phe
    50                  55                  60

Gln Gly Pro Glu Asp Ala Lys Asn Ile Lys Lys Gly Pro Ala Pro Phe
```

```
                65                  70                  75                  80
Tyr Pro Leu Glu Asp Gly Thr Ala Gly Glu Gln Leu His Lys Ala Met
                    85                  90                  95
Lys Arg Tyr Ala Leu Val Pro Gly Thr Ile Ala Phe Thr Asp Ala His
                100                 105                 110
Ile Glu Val Asn Ile Thr Tyr Ala Glu Tyr Phe Glu Met Ser Val Arg
                115                 120                 125
Leu Ala Glu Ala Met Lys Arg Tyr Gly Leu Asn Thr Asn His Arg Ile
130                 135                 140
Val Val Cys Ser Glu Asn Ser Leu Gln Phe Phe Met Pro Val Leu Gly
145                 150                 155                 160
Ala Leu Phe Ile Gly Val Ala Val Ala Pro Ala Asn Asp Ile Tyr Asn
                165                 170                 175
Glu Arg Glu Leu Leu Asn Ser Met Asn Ile Ser Gln Pro Thr Val Val
                180                 185                 190
Phe Val Ser Lys Lys Gly Leu Gln Lys Ile Leu Asn Val Gln Lys Lys
                195                 200                 205
Leu Pro Ile Ile Gln Lys Ile Ile Met Asp Ser Lys Thr Asp Tyr
210                 215                 220
Gln Gly Phe Gln Ser Met Tyr Thr Phe Val Thr Ser His Leu Pro Pro
225                 230                 235                 240
Gly Phe Asn Glu Tyr Asp Phe Val Pro Glu Ser Phe Asp Arg Asp Lys
                245                 250                 255
Thr Ile Ala Leu Ile Met Asn Ser Ser Gly Ser Thr Gly Leu Pro Lys
                260                 265                 270
Gly Val Ala Leu Pro His Arg Thr Ala Cys Val Arg Phe Ser His Ala
                275                 280                 285
Arg Asp Pro Ile Phe Gly Asn Gln Ile Ile Pro Asp Thr Ala Ile Leu
                290                 295                 300
Ser Val Val Pro Phe His His Gly Phe Gly Met Phe Thr Thr Leu Gly
305                 310                 315                 320
Tyr Leu Ile Cys Gly Phe Arg Val Val Leu Met Tyr Arg Phe Glu Glu
                325                 330                 335
Glu Leu Phe Leu Arg Ser Leu Gln Asp Tyr Lys Ile Gln Ser Ala Leu
                340                 345                 350
Leu Val Pro Thr Leu Phe Ser Phe Phe Ala Lys Ser Thr Leu Ile Asp
                355                 360                 365
Lys Tyr Asp Leu Ser Asn Leu His Glu Ile Ala Ser Gly Gly Ala Pro
                370                 375                 380
Leu Ser Lys Glu Val Gly Glu Ala Val Ala Lys Arg Phe His Leu Pro
385                 390                 395                 400
Gly Ile Arg Gln Gly Tyr Gly Leu Thr Glu Thr Thr Ser Ala Ile Leu
                405                 410                 415
Ile Thr Pro Glu Gly Asp Asp Lys Pro Gly Ala Val Gly Lys Val Val
                420                 425                 430
Pro Phe Phe Glu Ala Lys Val Val Asp Leu Asp Thr Gly Lys Thr Leu
                435                 440                 445
Gly Val Asn Gln Arg Gly Glu Leu Cys Val Arg Gly Pro Met Ile Met
                450                 455                 460
Ser Gly Tyr Val Asn Asn Pro Glu Ala Thr Asn Ala Leu Ile Asp Lys
465                 470                 475                 480
Asp Gly Trp Leu His Ser Gly Asp Ile Ala Tyr Trp Asp Glu Asp Glu
                485                 490                 495
```

```
His Phe Phe Ile Val Asp Arg Leu Lys Ser Leu Ile Lys Tyr Lys Gly
                500                 505                 510

Tyr Gln Val Ala Pro Ala Glu Leu Glu Ser Ile Leu Leu Gln His Pro
            515                 520                 525

Asn Ile Phe Asp Ala Gly Val Ala Gly Leu Pro Asp Asp Asp Ala Gly
        530                 535                 540

Glu Leu Pro Ala Ala Val Val Leu Glu His Gly Lys Thr Met Thr
545                 550                 555                 560

Glu Lys Glu Ile Val Asp Tyr Val Ala Ser Gln Val Thr Thr Ala Lys
                565                 570                 575

Lys Leu Arg Gly Gly Val Val Phe Val Asp Glu Val Pro Lys Gly Leu
            580                 585                 590

Thr Gly Lys Leu Asp Ala Arg Lys Ile Arg Glu Ile Leu Ile Lys Ala
        595                 600                 605

Lys Lys Gly Gly Lys
        610

<210> SEQ ID NO 24
<211> LENGTH: 535
<212> TYPE: PRT
<213> ORGANISM: Artificial Sequence
<220> FEATURE:
<223> OTHER INFORMATION: Synthetic sequence DED-HRV3C

<400> SEQUENCE: 24

Met Asp Tyr Lys Asp Asp Asp Lys Gly Met Ala Ser Asp Leu Ser
1               5                   10                  15

Asn Val Glu Gly Lys Thr Gly Asn Ala Thr Asp Glu Glu Glu Glu
            20                  25                  30

Glu Glu Glu Glu Glu Glu Asp Asp Asp Asp Asp Asp Asp
        35                  40                  45

Asp Asp Asp Glu Asp Ser Gly Ala Glu Ile Gln Asp Asp Glu Glu
    50                  55                  60

Gly Phe Asp Asp Glu Glu Glu Phe Asp Asp Asp Asp Glu His
65              70                  75                  80

Asp Asp Asp Asp Leu Glu Asn Glu Glu Asn Glu Leu Glu Glu Leu Glu
                85                  90                  95

Glu Arg Val Glu Ala Arg Lys Lys Met His His His His His Ser
            100                 105                 110

Ser Gly Met Ser Pro Ile Leu Gly Tyr Trp Lys Ile Lys Gly Leu Val
        115                 120                 125

Gln Pro Thr Arg Leu Leu Leu Glu Tyr Leu Glu Glu Lys Tyr Glu Glu
    130                 135                 140

His Leu Tyr Glu Arg Asp Glu Gly Asp Lys Trp Arg Asn Lys Lys Phe
145                 150                 155                 160

Glu Leu Gly Leu Glu Phe Pro Asn Leu Pro Tyr Tyr Ile Asp Gly Asp
                165                 170                 175

Val Lys Leu Thr Gln Ser Met Ala Ile Ile Arg Tyr Ile Ala Asp Lys
            180                 185                 190

His Asn Met Leu Gly Gly Cys Pro Lys Glu Arg Ala Glu Ile Ser Met
        195                 200                 205

Leu Glu Gly Ala Val Leu Asp Ile Arg Tyr Gly Val Ser Arg Ile Ala
    210                 215                 220

Tyr Ser Lys Asp Phe Glu Thr Leu Lys Val Asp Phe Leu Ser Lys Leu
225                 230                 235                 240
```

```
Pro Glu Met Leu Lys Met Phe Glu Asp Arg Leu Cys His Lys Thr Tyr
            245                 250                 255

Leu Asn Gly Asp His Val Thr His Pro Asp Phe Met Leu Tyr Asp Ala
        260                 265                 270

Leu Asp Val Val Leu Tyr Met Asp Pro Met Cys Leu Asp Ala Phe Pro
    275                 280                 285

Lys Leu Val Cys Phe Lys Lys Arg Ile Glu Ala Ile Pro Gln Ile Asp
290                 295                 300

Lys Tyr Leu Lys Ser Ser Lys Tyr Ile Ala Trp Pro Leu Gln Gly Trp
305                 310                 315                 320

Gln Ala Thr Phe Gly Gly Gly Asp His Pro Pro Lys Ser Asp Leu Val
            325                 330                 335

Pro Arg Gly Ser Pro Glu Phe Pro Gly Arg Leu Glu Arg Pro His Arg
        340                 345                 350

Asp Gly Pro Asn Thr Glu Phe Ala Leu Ser Leu Leu Arg Lys Asn Ile
    355                 360                 365

Met Thr Ile Thr Thr Ser Lys Gly Glu Phe Thr Gly Leu Gly Ile His
370                 375                 380

Asp Arg Val Cys Val Ile Pro Thr His Ala Gln Pro Gly Asp Asp Val
385                 390                 395                 400

Leu Val Asn Gly Gln Lys Ile Arg Val Lys Asp Lys Tyr Lys Leu Val
            405                 410                 415

Asp Pro Glu Asn Ile Asn Leu Glu Leu Thr Val Leu Thr Leu Asp Arg
        420                 425                 430

Asn Glu Lys Phe Arg Asp Ile Arg Gly Phe Ile Ser Glu Asp Leu Glu
    435                 440                 445

Gly Val Asp Ala Thr Leu Val Val His Ser Asn Asn Phe Thr Asn Thr
450                 455                 460

Ile Leu Glu Val Gly Pro Val Thr Met Ala Gly Leu Ile Asn Leu Ser
465                 470                 475                 480

Ser Thr Pro Thr Asn Arg Met Ile Arg Tyr Asp Tyr Ala Thr Lys Thr
            485                 490                 495

Gly Gln Cys Gly Gly Val Leu Cys Ala Thr Gly Lys Ile Phe Gly Ile
        500                 505                 510

His Val Gly Gly Asn Gly Arg Gln Gly Phe Ser Ala Gln Leu Lys Lys
    515                 520                 525

Gln Tyr Phe Val Glu Lys Gln
    530                 535

<210> SEQ ID NO 25
<211> LENGTH: 78
<212> TYPE: DNA
<213> ORGANISM: Artificial Sequence
<220> FEATURE:
<223> OTHER INFORMATION: Synthetic sequence DE12

<400> SEQUENCE: 25
gatgacaaag gtatggctag cgaggaggaa gaggaagaag atgatgatga tgacgacgct      60
agcctggaag ttctgttc                                                   78

<210> SEQ ID NO 26
<211> LENGTH: 78
<212> TYPE: DNA
<213> ORGANISM: Artificial Sequence
<220> FEATURE:
<223> OTHER INFORMATION: Synthetic sequence DE12
```

<400> SEQUENCE: 26
gaacagaact tccaggctag cgtcgtcatc atcatcatct tcttcctctt cctcctcgct       60
agccatacct tgtcatc                                                     78

<210> SEQ ID NO 27
<211> LENGTH: 30
<212> TYPE: DNA
<213> ORGANISM: Artificial Sequence
<220> FEATURE:
<223> OTHER INFORMATION: Synthetic sequence primer1

<400> SEQUENCE: 27
cgatacaaat ggaaataata accatctcgc                                       30

<210> SEQ ID NO 28
<211> LENGTH: 30
<212> TYPE: DNA
<213> ORGANISM: Artificial Sequence
<220> FEATURE:
<223> OTHER INFORMATION: Synthetic sequence primer2

<400> SEQUENCE: 28
cgcacagaat ctaacgctta ataaatgtac                                       30

<210> SEQ ID NO 29
<211> LENGTH: 825
<212> TYPE: DNA
<213> ORGANISM: Artificial Sequence
<220> FEATURE:
<223> OTHER INFORMATION: Synthetic sequence NQ01

<400> SEQUENCE: 29
atggtgggac gccgtgctct gatcgtgctc gctcactcgg aaagaacatc gttcaactac       60
gctatgaagg aggctgctgc cgctgccctg aagaagaagg ctgggaggt ggtcgaatcc      120 gacttgtacg ctatgaactt caaccccatc atctctcgta aggacatcac cggcaagctg      180
aaggatccag ccaacttcca gtacccggct gagtcagttt tggcctacaa ggaaggccac      240
ctgtcgcctg acatcgtggc tgagcaaaag aagctcgaag ctgccgattt ggttatcttc      300
cagttcccct tgcaatggtt cggtgtgcct gctatcctga agggctggtt cgagagggtc      360
ttcatcggag aattcgccta cacttacgct gccatgtacg acaagggtcc attcagatcg      420
aagaaggccg tcctgtccat caccactggt ggcagcggat caatgtacag cctccaggga      480
atccacggtg acatgaacgt catcctgtgg ccgatccaat ctggcatcct ccacttctgc      540
ggattccagg tgttggagcc acaactgaca tactccatcg acacacccc agctgacgct      600 cgtatccaga tcctcgaagg atggaagaag cgcttggaga acatctggga cgaaactccc      660
ttgtacttcg ctccttcctc tctgttcgat ctcaacttcc aggccggttt cctcatgaag      720
aaggaggtcc aagacgagga aaagaacaag aagttcggcc tgtctgttgg acaccacctc      780
ggcaagagca tccccacaga taaccagatc aaggctagga agtaa                     825

<210> SEQ ID NO 30
<211> LENGTH: 30
<212> TYPE: DNA
<213> ORGANISM: Artificial Sequence
<220> FEATURE:
<223> OTHER INFORMATION: Synthetic sequence primer3F

<400> SEQUENCE: 30
ctgttccagg gtcccatggt gggacgccgt                                         30

<210> SEQ ID NO 31
<211> LENGTH: 36
<212> TYPE: DNA
<213> ORGANISM: Artificial Sequence
<220> FEATURE:
<223> OTHER INFORMATION: Synthetic sequence primer3R

<400> SEQUENCE: 31
ggagctcgaa ttcccttact tcctagcctt gatctg                                  36

<210> SEQ ID NO 32
<211> LENGTH: 96
<212> TYPE: DNA
<213> ORGANISM: Artificial Sequence
<220> FEATURE:
<223> OTHER INFORMATION: Synthetic sequence DE18

<400> SEQUENCE: 32
gatgacaaag gtatggctag cgaagaagag gaggaggaag aggaagaaga tgatgatgat        60
gacgacgacg acgacgctag cctggaagtt ctgttc                                  96

<210> SEQ ID NO 33
<211> LENGTH: 96
<212> TYPE: DNA
<213> ORGANISM: Artificial Sequence
<220> FEATURE:
<223> OTHER INFORMATION: Synthetic sequence DE18

<400> SEQUENCE: 33
gaacagaact tccaggctag cgtcgtcgtc gtcgtcatca tcatcatctt cttcctcttc        60
ctcctcctct tcttcgctag ccatacctttg tcatc                                  96

<210> SEQ ID NO 34
<211> LENGTH: 273
<212> TYPE: DNA
<213> ORGANISM: Artificial Sequence
<220> FEATURE:
<223> OTHER INFORMATION: Synthetic sequence DED

<400> SEQUENCE: 34
gatctaagta atgtggaagg taagacagga aatgcaacag atgaagagga ggaagaagag        60
gaggaggaag aggaagaaga tgatgatgat gacgacgacg acgacgatga tgatgaagac       120
tctggagctg agatacaaga tgatgatgag gaaggttttg atgatgaaga ggaatttgat       180
gatgacgatg atgatgaaca tgatgatgat gatcttgaga atgaggaaaa cgaactggaa       240
gagttggaag agagggtaga agccaggaag aaa                                    273

<210> SEQ ID NO 35
<211> LENGTH: 34
<212> TYPE: DNA
<213> ORGANISM: Artificial Sequence
<220> FEATURE:
<223> OTHER INFORMATION: Synthetic sequence primer4F

<400> SEQUENCE: 35
aatagatctt ggtacccatg gaagaggagg aaga                                    34

<210> SEQ ID NO 36
<211> LENGTH: 63
<212> TYPE: DNA
<213> ORGANISM: Artificial Sequence
<220> FEATURE:
<223> OTHER INFORMATION: Synthetic sequence primer4R

<400> SEQUENCE: 36
ggagctcgaa ttcccgggac cctggaacag aacttccagg gtacctttat catcatcgtc    60
gtc    63

<210> SEQ ID NO 37
<211> LENGTH: 132
<212> TYPE: DNA
<213> ORGANISM: Artificial Sequence
<220> FEATURE:
<223> OTHER INFORMATION: Synthetic sequence DE30

<400> SEQUENCE: 37
gaacagaact tccaggctag catcatcatc gtcgtcgtcg tcgtcatcat catcatcgtc    60
gtcgtcctct tcctcttctt cctcttcctc ctcctcttct tcctcctctt cgctagccat   120
acctttgtca tc   132

<210> SEQ ID NO 38
<211> LENGTH: 132
<212> TYPE: DNA
<213> ORGANISM: Artificial Sequence
<220> FEATURE:
<223> OTHER INFORMATION: Synthetic sequence DE30

<400> SEQUENCE: 38
gatgacaaag gtatggctag cgaagaggag gaagaagagg aggaggaaga ggaagaagag    60
gaagaggacg acgacgatga tgatgatgac gacgacgacg acgatgatga tgctagcctg   120
gaagttctgt tc   132

<210> SEQ ID NO 39
<211> LENGTH: 150
<212> TYPE: DNA
<213> ORGANISM: Artificial Sequence
<220> FEATURE:
<223> OTHER INFORMATION: Synthetic sequence DE36

<400> SEQUENCE: 39
gaacagaact tccaggctag catcatcatc gtcgtcgtcg tcgtcatcat catcatcgtc    60
gtcgtcgtcg tcgtcctctt cctcctcttc ctcttcttcc tcttcctcct cctcttcttc   120
ctcctcttcg ctagccatac ctttgtcatc   150

<210> SEQ ID NO 40
<211> LENGTH: 150
<212> TYPE: DNA
<213> ORGANISM: Artificial Sequence
<220> FEATURE:
<223> OTHER INFORMATION: Synthetic sequence DE36

<400> SEQUENCE: 40
gatgacaaag gtatggctag cgaagaggag gaagaagagg aggaggaaga ggaagaagag    60
gaagaggagg aagaggacga cgacgacgac gacgatgatg atgatgacga cgacgacgac   120
gatgatgatg ctagcctgga agttctgttc   150

<210> SEQ ID NO 41
<211> LENGTH: 36
<212> TYPE: DNA
<213> ORGANISM: Artificial Sequence
<220> FEATURE:

<223> OTHER INFORMATION: Synthetic sequence primer5F

<400> SEQUENCE: 41
caaaggtatg gctagcgatc taagtaatgt ggaagg            36

<210> SEQ ID NO 42
<211> LENGTH: 35
<212> TYPE: DNA
<213> ORGANISM: Artificial Sequence
<220> FEATURE:
<223> OTHER INFORMATION: Synthetic sequence primer5R

<400> SEQUENCE: 42
gaacttccag gctagctttc ttcctggctt ctacc            35

<210> SEQ ID NO 43
<211> LENGTH: 38
<212> TYPE: DNA
<213> ORGANISM: Artificial Sequence
<220> FEATURE:
<223> OTHER INFORMATION: Synthetic sequence primer6F

<400> SEQUENCE: 43
gacaaaggta tggctagcga tctaagtaat gtggaagg         38

<210> SEQ ID NO 44
<211> LENGTH: 37
<212> TYPE: DNA
<213> ORGANISM: Artificial Sequence
<220> FEATURE:
<223> OTHER INFORMATION: Synthetic sequence primer6R

<400> SEQUENCE: 44
ggaacagaac ttccaggcta gcctcagctc cagagtc          37

<210> SEQ ID NO 45
<211> LENGTH: 114
<212> TYPE: DNA
<213> ORGANISM: Artificial Sequence
<220> FEATURE:
<223> OTHER INFORMATION: Synthetic sequence EO24

<400> SEQUENCE: 45
gatgacaaag gtatggctag cgaagaggag gaagaagagg aggaggaaga ggaagaagaa      60
gaggaggaag aagaggagga ggaagaggaa gaagctagcc tggaagttct gttc            114

<210> SEQ ID NO 46
<211> LENGTH: 114
<212> TYPE: DNA
<213> ORGANISM: Artificial Sequence
<220> FEATURE:
<223> OTHER INFORMATION: Synthetic sequence EO24

<400> SEQUENCE: 46
gaacagaact tccaggctag cttcttcctc ttcctcctcc tcttcttcct cctcttcttc      60
ttcctcttcc tcctcctctt cttcctcctc ttcgctagcc atacctttgt catc            114

<210> SEQ ID NO 47
<211> LENGTH: 35
<212> TYPE: DNA
<213> ORGANISM: Artificial Sequence
<220> FEATURE:
<223> OTHER INFORMATION: Synthetic sequence primer7F

<400> SEQUENCE: 47
gttccagggt ccagctagcg atctaagtaa tgtgg                                  35

<210> SEQ ID NO 48
<211> LENGTH: 34
<212> TYPE: DNA
<213> ORGANISM: Artificial Sequence
<220> FEATURE:
<223> OTHER INFORMATION: Synthetic sequence primer7R

<400> SEQUENCE: 48
cgtccttgta gtcgctagct ttcttcctgg cttc                                   34

<210> SEQ ID NO 49
<211> LENGTH: 33
<212> TYPE: DNA
<213> ORGANISM: Artificial Sequence
<220> FEATURE:
<223> OTHER INFORMATION: Synthetic sequence primer8F

<400> SEQUENCE: 49
cctataaata gatctcccat ggtgggacgc cgt                                    33

<210> SEQ ID NO 50
<211> LENGTH: 36
<212> TYPE: DNA
<213> ORGANISM: Artificial Sequence
<220> FEATURE:
<223> OTHER INFORMATION: Synthetic sequence primer8R

<400> SEQUENCE: 50
gaacagaact tccagcccct tcctagcctt gatctg                                 36

<210> SEQ ID NO 51
<211> LENGTH: 39
<212> TYPE: DNA
<213> ORGANISM: Artificial Sequence
<220> FEATURE:
<223> OTHER INFORMATION: Synthetic sequence primer9F

<400> SEQUENCE: 51
gttccagggt ccagctagcg atctaagtaa tgtggaagg                              39

<210> SEQ ID NO 52
<211> LENGTH: 37
<212> TYPE: DNA
<213> ORGANISM: Artificial Sequence
<220> FEATURE:
<223> OTHER INFORMATION: Synthetic sequence primer9R

<400> SEQUENCE: 52
catcgtcctt gtagtcgcta gcctcagctc cagagtc                                37

<210> SEQ ID NO 53
<211> LENGTH: 1638
<212> TYPE: DNA
<213> ORGANISM: Artificial Sequence
<220> FEATURE:
<223> OTHER INFORMATION: Synthetic luciferase sequence

<400> SEQUENCE: 53
gaagacgcca aaaacataaa gaaaggcccg gcgccattct atcctctaga ggatggaacc       60
gctggagagc aactgcataa ggctatgaag agatacgccc tggttcctgg aacaattgct      120
tttacagatg cacatatcga ggtgaacatc acgtacgcgg aatacttcga aatgtccgtt      180

```
cggttggcag aagctatgaa acgatatggg ctgaatacaa atcacagaat cgtcgtatgc    240
agtgaaaact ctcttcaatt ctttatgccg gtgttgggcg cgttatttat cggagttgca    300
gttgcgcccg cgaacgacat ttataatgaa cgtgaattgc tcaacagtat gaacatttcg    360
cagcctaccg tagtgtttgt ttccaaaaag gggttgcaaa aaattttgaa cgtgcaaaaa    420
aaattaccaa taatccagaa aattattatc atggattcta aaacggatta ccagggattt    480
cagtcgatgt acacgttcgt cacatctcat ctacctcccg gttttaatga atacgatttt    540
gtaccagagt cctttgatcg tgacaaaaca attgcactga taatgaattc ctctggatct    600
actgggttac ctaaggggtgt ggcccttccg catagaactg cctgcgtcag attctcgcat    660
gccagagatc ctattttggg caatcaaatc attccggata ctgcgatttt aagtgttgtt    720
ccattccatc acggttttgg aatgtttact acactcggat atttgatatg tggatttcga    780
gtcgtcttaa tgtatagatt tgaagaagag ctgttttac gatcccttca ggattacaaa    840
attcaaagtg cgttgctagt accaacccta ttttcattct tcgccaaaag cactctgatt    900
gacaaatacg atttatctaa tttacacgaa attgcttctg gggcgcacc tctttcgaaa    960 gaagtcgggg aagcggttgc aaaacgcttc catcttccag ggatacgaca aggatatggg   1020
ctcactgaga ctacatcagc tattctgatt cacccgagg gggatgataa accgggcgcg   1080
gtcggtaaag ttgttccatt ttttgaagcg aaggttgtgg atctggatac cgggaaaacg   1140
ctgggcgtta atcagagagg cgaattatgt gtcagaggac ctatgattat gtccggttat   1200
gtaaacaatc cggaagcgac caacgccttg attgacaagg atggatggct acattctgga   1260
gacatagctt actgggacga agacgaacac ttcttcatag ttgaccgctt gaagtctta   1320 attaaataca aaggatatca ggtggccccc gctgaattgg aatcgatatt gttacaacac   1380
cccaacatct tcgacgcggg cgtggcaggt cttcccgacg atgacgccgg tgaacttccc   1440
gccgccgttg ttgttttgga gcacggaaag acgatgacgg aaaaagagat cgtggattac   1500
gtcgccagtc aagtaacaac cgcgaaaaag ttgcgcggag gagttgtgtt tgtggacgaa   1560
gtaccgaaag gtcttaccgg aaaactcgac gcaagaaaaa tcagagagat cctcataaag   1620
gccaagaagg gcggaaag                                                  1638

<210> SEQ ID NO 54
<211> LENGTH: 30
<212> TYPE: DNA
<213> ORGANISM: Artificial Sequence
<220> FEATURE:
<223> OTHER INFORMATION: Synthetic sequence primer10F

<400> SEQUENCE: 54
ctgttccagg gtcccgaaga cgccaaaaac                                      30

<210> SEQ ID NO 55
<211> LENGTH: 35
<212> TYPE: DNA
<213> ORGANISM: Artificial Sequence
<220> FEATURE:
<223> OTHER INFORMATION: Synthetic sequence primer10R

<400> SEQUENCE: 55
ggagctcgaa ttcccttact ttccgccctt cttgg                                35

<210> SEQ ID NO 56
<211> LENGTH: 1296
<212> TYPE: DNA
<213> ORGANISM: Artificial Sequence
```

<220> FEATURE:
<223> OTHER INFORMATION: Synthetic sequence HRV3C

<400> SEQUENCE: 56

```
atgcaccacc accatcatca ttcgagcggt atgagcccca ttttgggggta ttggaaaatc    60
aaaggtctgg ttcaaccaac ccggctcctg cttgaatatc ttgaagagaa atacgaagag   120
catctgtatg aacgtgacga aggcgataaa tggcgcaata agaagtttga acttggcctg   180
gagtttccga acttgccgta ttacattgat ggcgatgtga aactgacaca gtctatggcg   240
attattcgct atattgcgga caaacacaac atgttaggcg gttgcccgaa agaacgtgcg   300
gaaatctcaa tgttagaagg ggctgttctc gatattcgct atggcgtgtc tcgtatcgca   360
tacagtaaag actttgaaac gctgaaagtc gattttcttt cgaaattgcc ggagatgctg   420
aaaatgttcg aagatcggtt gtgccacaaa acgtatctga acggggatca tgtcacccat   480
ccggatttca tgttgtacga tgctctggat gtggtgctgt atatggaccc aatgtgcttg   540
gacgcgtttc caaagctggt gtgtttcaag aaacgcattg aggccattcc gcagattgat   600
aaatacctga aagctcgaa atatattgcg tggcctctgc agggttggca agccaccttt   660
ggtggcggag atcaccctcc gaaaagcgat ctggtcccgc gtgggagtcc tgaatttcca   720
ggtcgccttg agcgcccgca tcgtgatggt ccgaacacgg aattcgcact gtccctcctg   780
cgcaagaaca ttatgacaat caccacgagc aaaggcgaat tcactggact gggaatccat   840
gatcgcgtgt gtgttattcc cacccatgca cagcctggtg atgacgtcct ggtaaatggc   900
cagaaaatcc gcgttaaaga caaatacaaa ctggtagacc cggaaaacat caatctcgaa   960
ctgaccgtgt taaccttaga ccgtaacgag aaatttcgcg acattcgcgg tttcatttcc  1020
gaggacctcg aaggtgtgga tgcaacgctg gtagtgcatt ccaacaattt cacgaatacc  1080
atcctggaag ttggcccggt tacaatggcc ggcttaatca acctgtctag tactcccacc  1140
aatcgtatga ttcgctatga ttacgcgacc aagactggcc aatgtggtgg agtcttatgc  1200
gctactggca aaatctttgg gatccacgtt ggtggcaatg gccgtcaggg cttttcagcc  1260
caactgaaga aacagtactt cgtagaaaag cagtaa                             1296
```

<210> SEQ ID NO 57
<211> LENGTH: 42
<212> TYPE: DNA
<213> ORGANISM: Artificial Sequence
<220> FEATURE:
<223> OTHER INFORMATION: Synthetic sequence primer11F

<400> SEQUENCE: 57

```
cgatgacaaa ggtatggcta gcgatctaag taatgtggaa gg                        42
```

<210> SEQ ID NO 58
<211> LENGTH: 39
<212> TYPE: DNA
<213> ORGANISM: Artificial Sequence
<220> FEATURE:
<223> OTHER INFORMATION: Synthetic sequence primer11R

<400> SEQUENCE: 58

```
gatgatggtg gtggtgcatt tcttcctgg cttctaccc                             39
```

<210> SEQ ID NO 59
<211> LENGTH: 39
<212> TYPE: DNA
<213> ORGANISM: Artificial Sequence
<220> FEATURE:

<223> OTHER INFORMATION: Synthetic sequence primer12F

<400> SEQUENCE: 59
gggtagaagc caggaagaaa atgcaccacc accatcatc                    39

<210> SEQ ID NO 60
<211> LENGTH: 44
<212> TYPE: DNA
<213> ORGANISM: Artificial Sequence
<220> FEATURE:
<223> OTHER INFORMATION: Synthetic sequence primer12R

<400> SEQUENCE: 60
ctcgaggagc tcgaattccc ttactgcttt tctacgaagt actg              44

<210> SEQ ID NO 61
<211> LENGTH: 45
<212> TYPE: DNA
<213> ORGANISM: Artificial Sequence
<220> FEATURE:
<223> OTHER INFORMATION: Synthetic sequence primer13F

<400> SEQUENCE: 61
ctttaagaag gagatataca tatggactac aaggacgacg atgac             45

<210> SEQ ID NO 62
<211> LENGTH: 45
<212> TYPE: DNA
<213> ORGANISM: Artificial Sequence
<220> FEATURE:
<223> OTHER INFORMATION: Synthetic sequence primer13R

<400> SEQUENCE: 62
ccaccagtca tgctagccat atgttactgc ttttctacga agtac             45

<210> SEQ ID NO 63
<211> LENGTH: 16
<212> TYPE: DNA
<213> ORGANISM: Artificial Sequence
<220> FEATURE:
<223> OTHER INFORMATION: Synthetic sequence primer14

<400> SEQUENCE: 63
atgcgtccgg cgtaga                                             16

<210> SEQ ID NO 64
<211> LENGTH: 18
<212> TYPE: DNA
<213> ORGANISM: Artificial Sequence
<220> FEATURE:
<223> OTHER INFORMATION: Synthetic sequence primer15

<400> SEQUENCE: 64
ccctcaagac ccgtttag                                           18

<210> SEQ ID NO 65
<211> LENGTH: 6
<212> TYPE: PRT
<213> ORGANISM: Artificial Sequence
<220> FEATURE:
<223> OTHER INFORMATION: Synthetic sequence DE6

<400> SEQUENCE: 65

Glu Glu Glu Asp Asp Asp
1               5

```
<210> SEQ ID NO 66
<211> LENGTH: 60
<212> TYPE: DNA
<213> ORGANISM: Artificial Sequence
<220> FEATURE:
<223> OTHER INFORMATION: Synthetic sequence DE6

<400> SEQUENCE: 66
gatgacaaag gtatggctag cgaggaagaa gatgatgatg ctagcctgga agttctgttc    60

<210> SEQ ID NO 67
<211> LENGTH: 60
<212> TYPE: DNA
<213> ORGANISM: Artificial Sequence
<220> FEATURE:
<223> OTHER INFORMATION: Synthetic sequence DE6

<400> SEQUENCE: 67
gaacagaact tccaggctag catcatcatc ttcttcctcg ctagccatac ctttgtcatc    60
```